(12) United States Patent
Williams et al.

(10) Patent No.: US 7,786,091 B2
(45) Date of Patent: Aug. 31, 2010

(54) COMPOSITIONS AND METHODS FOR AMELIORATING MYOSIN VIIA DEFECTS

(75) Inventors: David Williams, San Diego, CA (US); Xian-Jie Yang, Culver City, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/021,078

(22) Filed: Jan. 28, 2008

(65) Prior Publication Data

US 2009/0191155 A1    Jul. 30, 2009

(51) Int. Cl.
*A01N 43/04*    (2006.01)
*A61K 31/715*    (2006.01)

(52) U.S. Cl. ..................... 514/44; 424/93.21
(58) Field of Classification Search ............... 424/93.2, 424/93.21; 514/44
See application file for complete search history.

(56) References Cited

U.S. PATENT DOCUMENTS 6,808,923 B2 * 10/2004 Engelman et al. ......... 435/320.1
2004/0208847 A1 * 10/2004 Rolling et al. ............. 424/93.2

OTHER PUBLICATIONS

Miller (1995, FASEB J., vol. 9, pp. 190-199).*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, pp. 404-410).*
Hasson (PNAS, 1995, vol. 92, No. 21, p. 9815-9819).*
El-Amraoui et al., Human Molecular Genetics (1996) 5(8):1171-1178.
Hashimoto et al., Gene Therapy (2007)14:584-594.
Lillo et al., "Mouse Models for Usher Syndrome 1B", in Retinal Degenerations: Mechanisms and Experimental Therapy, La Vail et al., (eds.), Kluwer Academic/Plenum Publishers (2003) pp. 143-150.
Liu et al., Cell Motility and the Cytoskeleton (1997) 37:240-252.
Well et al., Nature (1995) 374:60-61.

* cited by examiner

*Primary Examiner*—Michael C. Wilson
(74) *Attorney, Agent, or Firm*—Gavrilovich, Dodd, Lindsey LLP; Gregory P Einhorn

(57) ABSTRACT

The invention provides compositions and methods for ameliorating defects in myosin VIIa (MYO7A) expression and/or function, including providing vectors for myosin VIIa expression and formulations comprising them, and methods of using them, for treating human retinitis pigmentosa (or retinal degeneration), and blindness and deafness such as that found in Usher syndrome. The invention provides in vivo gene therapy for ameliorating defects in myosin VIIa (MYO7A) expression and/or function, including compositions and methods for gene transfer of the human myosin VIIa (MYO7A) gene (the MYO7A gene.

20 Claims, 6 Drawing Sheets
(5 of 6 Drawing Sheet(s) Filed in Color)

COMPOSITIONS AND METHODS FOR AMELIORATING MYOSIN VIIA DEFECTS

FEDERAL FUNDING

This invention was produced in part using funds from the Federal government under USP1IS N11-1, NEI Grant No. 1 R03 EY014440-01; and grants FFB T-GT-0602-0217 and T-GT-0304-0252, National Institutes of Health. Accordingly, the Federal government has certain rights in this invention.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 220002072300Seqlist.txt | May 6, 2008 | 18,193 bytes |

TECHNICAL FIELD

This invention relates to molecular and cellular biology, biochemistry, molecular genetics, gene therapy, and pharmacology. The invention provides compositions and methods for ameliorating defects in myosin VIIa (MYO7A) expression and/or function, including providing vectors for myosin VIIa (MYO7A) expression and formulations comprising them, and methods of using them, for treating human retinitis pigmentosa (or retinal degeneration), and blindness and deafness such as that found in Usher syndrome. The invention provides in vivo gene therapy for ameliorating defects in myosin VIIa (MYO7A) expression and/or function, including compositions and methods for gene transfer of the human myosin VIIa (MYO7A) gene (the MYO7A gene).

BACKGROUND

Usher syndrome, or Usher's syndrome, is an inherited condition that is a leading cause of deaf-blindness. People born with this syndrome gradually become blind and deaf, usually by the age of thirty. In more severe cases, children and even infants may have significant impairment of their vision and hearing, as well as difficulties maintaining their balance, due to problems in the vestibular system. Usher syndrome is an autosomal recessive disorder of combined deafness and blindness resulting in one of the most debilitating forms of retinal degeneration, since it affects patients who already suffer from deafness. Usher type 1B is due to mutations in the MYO7A gene that encodes an unconventional myosin expressed in the RPE (retinal pigment epithelium) and photoreceptor cells, within the retina, plus other cells of the body, including the cochlear hair cells. Myo7a-null mice have mutant retinal phenotypes, including defects in phagosome and melanosome transport.

Mutations in the MYO7A gene account for approximately 60% of cases with a clinical diagnosis of Usher Syndrome Type I. Mutations in the USH2A gene accounts for approximately 80% of cases with a clinical diagnosis of Usher Syndrome Type II.

MYO7A has been reported to be double headed myosin. It consists of a conserved myosin motor domain, a neck region with 5 IQ motifs, a short coiled-coil domain, and a tail consisting of two repeats of a myosin tail homology domain (Myth4) and a band 4.1 ezrin/radaxin/moesin homology domain (FERM) separated by a poorly conserved S113 domain.

SUMMARY

The invention provides compositions and methods for ameliorating defects in myosin VIIa (MYO7A) expression and/or function, including ameliorating defects in myosin VIIa (MYO7A) expression and/or function due to genetic defects in MYO7a sequence. In one aspect, the invention provides exogenous nucleic acids that encode wild type, or functional, myosin VIIa (MYO7A) to cells, tissues, organs and/or individuals. Thus, the invention provides compositions and methods for ameliorating diseases and conditions caused or exacerbated by a defect in myosin VIIa (MYO7A) expression and/or function, including human retinitis pigmentosa (or retinal degeneration), and blindness and deafness such as that found in Usher syndrome.

In one aspect, the invention provides expression vehicles, such as vectors, for myosin VIIa expression in a cell, tissue, organ and/or individual, and formulations comprising them, and methods of using them, for ameliorating (e.g., treating) diseases and conditions caused or exacerbated by a defect in myosin VIIa (MYO7A) expression and/or function. Thus, the invention provides expression vehicles, such as vectors, for ameliorating (e.g., treating) human retinitis pigmentosa (or retinal degeneration), and blindness and deafness such as that found in Usher syndrome.

In another aspect, the invention provides compositions and methods for in vivo gene therapy for ameliorating defects in myosin VIIa (MYO7A) expression and/or function, including compositions and methods for gene transfer of the human myosin VIIa gene (the MYO7A gene).

The invention provides expression vehicles, e.g., vectors, expression cassettes, recombinant viruses and/or promoters, for inserting a myosin VIIa (MYO7A)-expressing nucleic acid into a cell, tissue, organ and/or individual. In one aspect of the invention, target sequences are inserted into a genome to facilitate stable integration of a construction of the invention into a genome; for example, target sequences can be inserted into a genome using a lentiviral feline immunodeficiency (FIV) vector for the transduction process.

Thus, the invention provides compositions and methods for gene therapy of retinitis pigmentosa (or retinal degeneration), and blindness and deafness such as that found in Usher syndrome. In one aspect, the invention provides expression vehicles, e.g., vectors, expression cassettes, recombinant viruses and/or promoters, formulations comprising the same, and methods for the gene transfer of a MYO7A gene, e.g., the human MYO7A gene. Exemplary expression vehicles, e.g., vectors, expression cassettes, recombinant viruses and/or promoters, are described and illustrated herein.

The invention provides methods of ameliorating or preventing blindness due to Usher 1B syndrome by inducing, upregulating or inserting a MYO7A activity in a photoreceptor cell or a retinal cell, comprising: (a) providing a lentiviral vector comprising: a human MYO7A-encoding nucleic acid; a promoter active in RPE cells, photoreceptor cells, and/or both RPE and photoreceptor cells; and, a chromatin insulator; and (b) inserting the lentiviral vector into the cell.

The invention provides methods for the treatment or amelioration of an ocular disease, comprising delivering to target cells in an eye of a subject in need of said treatment, a vector comprising a promoter in operable linkage with a polynucleotide sequence encoding a MYO7A protein, wherein the MYO7A protein is expressed in said target cells, thereby treating ocular disease in said subject.

The invention provides methods method for treatment or amelioration of blindness due to Usher 1B syndrome in a subject, comprising delivering to target cells in the eye of the subject, a vector comprising a promoter in operable linkage with a polynucleotide sequence encoding a MYO7A protein, wherein the MYO7A protein is expressed in said target cells thereby treating blindness in said subject.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

Like reference symbols in the various drawings indicate like elements.

The patent or application file contains at least one drawing executed in color. Copies of this patent or patent application publication with color drawing(s) will be provided by the Office upon request and payment of the necessary fee.

Figure 1:
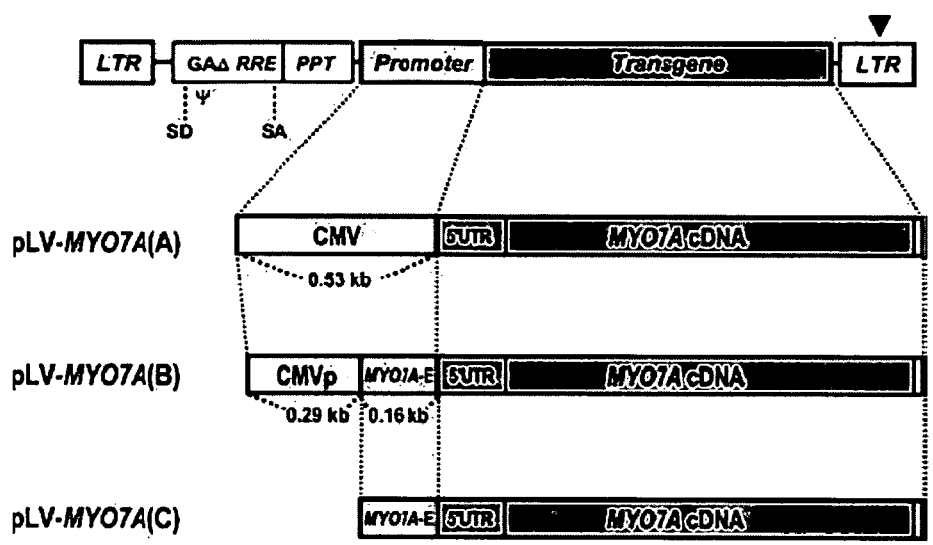
FIG. 1 is a schematic drawing of lentiviral vectors encoding the human MYO7A cDNA. The LV-MYO7A(A) vector encodes the CMV promoter upstream of the human MYO7A cDNA. The LV-MYO7A(B) vector contains a chimeric promoter, consisting of a partial CMV promoter (CMVp) and a 160-bp sequence from the human MYO7A promoter (MYO7A-E). The LV-MYO7A(C) encodes the 160-bp "MYO7A-E" fragment only. LTR, long terminal repeat; GAΔ, partial HIV1 GAG gene; RRE, Rev responsive element; PPT, polypurine track; ψ, viral packaging sequence; SD, splice donor; SA, splice acceptor. The arrowhead indicates the deletion within the 3' LTR that causes self-inactivation of the viral LTR enhancer upon integration.

or LV-MYO7A(A) (Mut+A). The lack of pigmentation in the last indicates a large loss of cells.

DETAILED DESCRIPTION

The invention provides compositions and methods for ameliorating defects in myosin VIIa (MYO7A) expression and/or function, including providing nucleic acids for myosin VIIa expression, including expression vehicles such as vectors, recombinant viruses and the like. The invention provides pharmaceutical compositions, e.g., formulations, comprising these nucleic acids and expression vehicles, and methods of using them, e.g., for ameliorating (e.g., treating) a defect in myosin VIIa (MYO7A) expression and/or function. The invention provides compositions and methods for ameliorating (e.g., treating) human retinitis pigmentosa (or retinal degeneration), and blindness and deafness such as that found in Usher syndrome.

In one aspect, the invention provides compositions and methods for in vivo gene therapy for ameliorating defects in myosin VIIa (MYO7A) expression and/or function, including compositions and methods for gene transfer of the human myosin VIIa gene (the human MYO7A gene).

In one aspect, the invention provides for compositions and methods for constructing and using these nucleic acids, expression vehicles (e.g., vectors) and pharmaceutical formulations of the invention express a functional MYO7A, e.g., express a human recombinant MYO7A gene. This expression can be in vivo, ex vivo or in vitro, for gene therapy or for investigatory or drug screening use, e.g., in a myo7a-null primary RPE cells.

In alternative aspects, the invention provides prophylactic, palliative and or corrective gene therapy for MYO7A expression and/or function defects, e.g., for treating and/or preventing blindness, and/or for treating, preventing and/or correcting deafness in individuals with a MYO7A genetic defect, e.g., an Usher syndrome type 1B, which is an inherited recessive disorder caused by mutations in the MYO7A gene. The Usher 1B patients are born deaf, and later develop retinal degeneration (retinitis pigmentosa) in their teens—thus, in alternative aspects, the compositions of the invention are used to prevent and/or ameliorate (treat) these conditions.

The data presented herein demonstrates that MYO7A cDNA can be delivered to retinas in vivo; a predictive animal model using cultured primary RPE cells of Myo7a-null mice, using a lentiviral vector was used. Using a promoter containing elements of the native MYO7A promoter, appropriate levels of myosin VIIa were obtained in the RPE cells, correction of mutant phenotypes—melanosome motility and phagosome digestion in cultured RPE cells, and melanosome localization and opsin clearance from the connecting cilium in vivo—was achieved.

Nucleic Acids

The invention provides compositions and methods comprising use of a MYO7A-expressing nucleic acid, such as a MYO7A gene or MYO7A-encoding message. The invention provides expression constructs, including expression cassettes, vectors, recombinant viruses such as adenoviruses and/or lentiviruses; and/or promoters operatively linked to a MYO7A-expressing nucleic acid, such as a MYO7A gene. In one aspect, the invention provides expression constructs operably linked to a myo7a coding sequence, e.g., the MYO7A gene.

In one aspect, nucleic acids or nucleic acid sequences used to practice this invention include oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin. In one aspect, nucleic acids or nucleic acid sequences used to practice this invention include oligonucleotides containing known analogues of natural nucleotides, naturally occurring nucleic acids, synthetic nucleic acids and/or recombinant nucleic acids. In one aspect, nucleic acids or nucleic acid sequences used to practice this invention encompass nucleic-acid-like structures with synthetic backbones, see e.g., Mata (1997) Toxicol. Appl. Pharmacol. 144: 189-197; Strauss-Soukup (1997) Biochemistry 36:8692-8698; Samstag (1996) Antisense Nucleic Acid Drug Dev 6:153-156.

In one aspect, the invention provides a MYO7A gene, and in one aspect the term "gene" can refer to any segment of nucleic acid associated with a biological function, e.g., MYO7A function. Thus, genes used to practice this invention include coding sequences and/or the regulatory sequences required for their expression. For example, a MYO7A gene can comprise a nucleic acid fragment that expresses mRNA, functional RNA, or specific protein (e.g., MYO7A), including regulatory sequences. Alternatively, genes used to practice this invention can also include non-expressed DNA segments that, for example, form recognition sequences for other proteins. Genes used to practice this invention can be obtained from a variety of sources, including cloning from a source of interest or synthesizing from known or predicted sequence information, and may include sequences designed to have desired parameters. Genes used to practice this invention include nucleic acid sequences comprising a segment of DNA involved in producing a transcription product (e.g., a message), which in turn is translated to produce a polypeptide chain, or regulates gene transcription, reproduction or stability. Genes used to practice this invention can include regions preceding and following the coding region, such as leader and trailer, promoters and enhancers, as well as, where applicable, intervening sequences (introns) between individual coding segments (exons).

In one aspect, nucleic acids used to practice this invention are operably linked to a promoter, e.g., there is a functional relationship between two or more nucleic acid (e.g., DNA) segments, e.g., a transcriptional regulator and a protein coding sequence. In one aspect, this comprises a functional relationship of transcriptional regulatory sequence to a transcribed myo7a sequence. In one aspect, a promoter is operably linked to a myo7a coding sequence, such as a human myo7a, and the promoter can stimulate or modulate the transcription of the coding sequence in an appropriate host cell or other expression system. In one aspect, a promoter transcriptional regulatory sequence that is operably linked to a transcribed myo7a sequence is physically contiguous to the transcribed sequence, i.e., they are cis-acting. In one aspect, some transcriptional regulatory sequences, such as enhancers, are not physically contiguous or located in close proximity to the MYO7A-coding sequences whose transcription they enhance.

Nucleic acids used to practice this invention can be operably linked to any promoter, which includes all sequences capable of driving transcription of a coding sequence in a cell, e.g., a plant cell or animal cell. Nucleic acids used to practice this invention can be operably linked to any control elements and/or regulatory sequences that are involved in regulating or modulating the timing and/or rate of transcription of a gene. For example, in one aspect a promoter is a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences can interact with proteins or other biomolecules to carry out (turn on/off, regulate, modulate, etc.) transcription. Nucleic acids used to practice this invention can be operably linked to any constitutive promoter, including those that drive expression continuously under most environmental conditions and states of development or cell differentiation; or, to any inducible or regulatable promoter, e.g., those that can direct expression of a nucleic acid, e.g., MYO7a, under the influence of environmental conditions or developmental conditions; examples of environmental conditions that may affect transcription by inducible promoters include anaerobic conditions, elevated temperature, drought, or the presence of light.

Nucleic acids used to practice this invention can be operably linked to any tissue-specific promoters, e.g., those that are transcriptional control elements that are only active in particular cells or tissues or organs, e.g., in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

Nucleic acids used to practice this invention can be operably linked to transcriptional control elements that overexpress a nucleic acid, e.g., MYO7A, e.g., overexpress the level of expression in a transfected or transgenic cell, or transgenic organism, that exceeds levels of expression in normal or untransformed cells or organisms.

Nucleic acids used to practice the invention, including the human MYO7A gene, and vectors comprising this or other nucleic acids can be made, isolated and/or manipulated by, e.g., cloning and expression of cDNA libraries, amplification of message or genomic DNA by PCR, and the like. In practicing the methods of the invention, homologous genes (e.g., MYO7A genes) can be modified by manipulating a template nucleic acid, as described herein. The invention can be practiced in conjunction with any method or protocol or device known in the art, which are well described in the scientific and patent literature.

The nucleic acids used to practice this invention, whether RNA, miRNA, siRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides or gene products (or nucleic acid molecules) generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by several well-known chemical synthesis techniques, as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth, Enzymol. 68:109; Beaucage (1981) Tetra. Lett. 22:1859; U.S. Pat. No. 4,458,066. Alternatively, nucleic acids can be obtained from commercial sources.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., Molecular Cloning: A Laboratory Manual ($2^{nd}$ 10 ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization with Nucleic Acid Probes, Part I. Theory and Nucleic Acid Preparation, Tijssen, ed. Elsevier, N.Y. (1993).

Another useful means of obtaining and manipulating nucleic acids used to practice this invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACS), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kem (1997) Biotechniques 23:120-124; cosmids, recombinant viruses, phages or plasmids.

In practicing the invention, nucleic acids of the invention or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

Known methods of PCR used to practice this invention include, e.g., methods using paired primers, nested primers, single specific primers, degenerate primers, gene-specific primers, vector-specific primers, partially mismatched primers, and the like.

Amplification reactions can also be used to quantify the amount of nucleic acid in a sample (such as the amount of message RNA (mRNA) in a cell sample), label the nucleic acid (e.g., to apply it to an array or a blot), detect the nucleic acid, or quantify the amount of a specific nucleic acid in a sample. In one aspect of the invention, mRNA isolated from a cell or a cDNA library is amplified. The skilled artisan can select and design suitable oligonucleotide amplification primers. Amplification methods are also well known in the art, and include, e.g., polymerase chain reaction, PCR (see, e.g., PCR Protocols, A Guide to Methods and Applications, ed. Innis, Academic Press, N. Y. (1990) and PCR Strategies (1995), ed. Innis, Academic Press, Inc., N. Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatclli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Ma Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683, 195 and 4,683,202; and Sooknanan (1995) Biotechnology 13:563-564.

In one aspect of the invention, a construct of the invention comprises a reporter or marker gene. The reporter or marker gene is used to monitor gene (e.g., MYO7A gene) expression. In one aspect, the reporter or marker gene is used to monitor gene suppression or silencing. In one aspect of the invention, the reporter gene is green fluorescent protein. Any compound, label, or gene that has a reporting or marking function can be used.

Host Cells

The invention provides cells comprising a myosin VIIa (MYO7A)-expressing nucleic acid for ex vivo and/or in vivo gene therapy for ameliorating defects in myosin VIIa (MYO7A) expression and/or function, e.g., for gene transfer of the human myosin VIIa gene (the MYO7A gene) to the cells. These cells can also be used in drug screening studies or for research.

In one aspect, cells of the invention are made by transformation, which can be the transfer of a nucleic acid fragment into the genome of a host cell, resulting in genetically stable inheritance. A host cell used to practice this invention can be a cell that has been transformed by an exogenous nucleic acid molecule. Host cells used to practice this invention containing the transformed nucleic acid fragments are referred to as "transgenic" cells, and organisms comprising transgenic cells are referred to as "transgenic organisms".

A host cell used to practice this invention can be "transformed", "transduced", "transgenic", and/or a "recombinant" host cell or organism into which a heterologous nucleic acid molecule (e.g., a MYO7A gene) has been introduced. The nucleic acid molecule used to practice this invention can be stably integrated into the genome, e.g., as described in Sambrook and Russell. For example, "transformed," "transformant," and "transgenic" cells have been through the transformation process and contain a foreign gene integrated into their chromosome. A host cell used to practice this invention can be untransformed, or a normal cell that has not been through the transformation process, but contains a myosin VIIa (MYO7A)-expressing nucleic acid.

In one aspect, the invention provides transfection of cells, i.e., the acquisition by a cell of new nucleic acid material by incorporation of added DNA, e.g., a MYO7A gene. Thus, transfection used to practice this invention can include the insertion of nucleic acid into a cell using physical or chemical methods. Any transfection techniques known to those of ordinary skill in the art can be used, including: calcium phosphate DNA co-precipitation; DEAE-dextran; electroporation; cationic liposome-mediated transfection; and tungsten particle-facilitated microparticle bombardment (Johnston (1990). Strontium phosphate DNA co-precipitation is also a transfection method.

In one aspect, the transduction of cells to practice this invention includes the process of transferring nucleic acid into a cell using a DNA or RNA virus. In one aspect, an RNA virus (i.e., a retrovirus) used to practice this invention for transferring a nucleic acid into a cell is a transducing chimeric retrovirus. Exogenous nucleic acid material contained within the retrovirus can be incorporated into the genome of the transduced cell. In one aspect, a cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

MYO7A and MYO7A Sequences

The invention provides nucleic acid constructs comprising a MYO7A-expressing sequence, e.g., a MYO7A-expressing message RNA or a MYO7A gene, e.g., a MYO7A nucleic acid sequence, including, for example Homo sapiens MYO-VIIA sequence as set forth in GenBank nos. U39226, U34227, AAB03679, O55208, and U55209; and/or the Mus MYOVIIa sequences as set forth in GenBank no. U81453; and/or the hsEST sequence as set forth in GenBank no. BE780659. In one aspect, MYO7A-expressing nucleic acids used to practice this invention include MYO7A genomic sequences, or fragments thereof, including coding or non-coding sequences, e.g., including introns, 5' or 3' non-coding sequences, and the like.

In one aspect, a MYO7A-expressing nucleic acid encodes a human MYO7A, such as (Genbank accession no. NP_000251):

(SEQ ID NO: 1)

```
   1  mvilqqgdhv wmdlrlgqef dvpigavvkl cdsgqvqvvd
      dednehwisp qnathikpmh 61  ptsvhgvedm irlgdlneag lirnlliryr dhliytytgs
      ilvavnpyql isiyspehir 121  qytnkkigem pphifaiadn cyfnmkrnsr dqcciisges
      gagktestkl ilqflaaisg 181  qhswieqqvl eatpileafg naktirndns srfgkyidih
      fnkrgaiega kieqylleks 241  rvcrqalder nyhvfycmle gmsedqkkkl glgqasdyny
      lamgncitce grvdsqeyan 301  irsamkvlmf tdtenweisk llaailhlgn lqyeartfen
      ldacevlfsp slataaslle 361  vnppdlmscl tsrtlitrge tvstplsreq aldvrdafvk
      giygrlfvwi vdkinaaiyk 421  ppsqdvknsr rsiglldifg fenfavnsfe qlcinfaneh
      lqqffvrhvf kleqeeydle 481  sidwlhieft dnqdaldmia nkpmniisli deeskfpkgt
      dttmlhklns qhklnanyip 541  pknnhetqfg inhfagivyy etqgfleknr dtlhgdiiql
      vhssrnkfik qifqadvamg 601  aetrkrsptl ssqfkrslel lmrtlgacqp ffvrcikpne
      fkkpmlfdrh lcvrqlrysg 661  mmetirirra gypirysfve fveryrvllp gvkpaykqgd
      lrgtcqrmae avlgthddwq 721  igktkiflkd hhdmllever dkaitdrvil lqkvirgfkd
      rsnflklkna atliqrhwrg 781  hncrknyglm rlgflrlqal hrsrklhqqy rlarqriiqf
      qarcraylvr kafrhrlwav 841  ltvqayargm iarrlhqrlr aeylwrleae kmrlaeeekl
      rkemsakkak eeaerkhqer 901  laqlaredae relkekeaar rkkelleqme rarhepvnhs
      dmvdkmfgfl gtsgglpgqe 961  gqapsgfedl ergrremvee dldaalplpd edeedlseyk
      fakfaatyfq gttthsytrr 1021  plkqpllyhd degdqlaala vwitilrfmg dlpepkyhta
      msdgsekipv mtkiyetlgk 1081  ktykrelqal qgegeaqlpe gqkkssvrhk lvhltlkkks
      klteevtkrl hdgestvqgn 1141  smledrptsn leklhfiign gilrpalrde iycqiskqlt
      hnpskssyar gwilvslcvg 1201  cfapsekfvk ylrnfihggp pgyapyceer lrrtfvngtr
      tqppswlelq atkskkpiml 1261  pvtfmdgttk tlltdsatta kelcnaladk islkdrfgfs
      lyialfdkvs slgsgsdhvm
```

-continued

```
1321    daisqceqya keqgaqerna pwrlffrkev ftpwhspsed
        nvatnhiyqq vvrgvkfgey 1381    rcekeddlae lasqqyfvdy gsemilerll nlvptyipdr
        eitplktlek waqlaiaahk 1441    kgiyaqrrtd aqkvkedvvs yarfkwpllf srfyeaykfs
        gpslpkndvi vavnwtgvyf 1501    vdeqeqvlle lsfpeimavs ssrgakttap sftlatikgd
        eytftssnae dirdlvvtfl 1561    eglrkrskyv valqdnpnpa geesgflsfa kgdliildhd
        tgeqvmnsgw anginertkq 1621    rgdfptdsvy vmptvtmppr eivalvtmtp dqrqdvvrll
        qlrtaepevr akpytleefs 1681    ydyfrpppkh tlsrvmvska rgkdrlwsht replkqallk
        kllgseelsq eaclafiavl 1741    kymgdypskr trsvneltdq ifegplkaep lkdeayvqil
        kqltdnhiry seergwellw 1801    lctglfppsn illphvqrfl qsrkhcplai dclqrlqkal
        rngsrkypph lveveaiqhk 1861    ttqifhkvyf pddtdeafev esstkakdfc qniatrlllk
        ssegfslfvk iadkvlsvpe 1921    ndfffdfvrh ltdwikkarp ikdgivpslt yqvffmkklw
        tttvpgkdpm adsifhyyqe 1981    lpkylrgyhk ctreevlqlg aliyrvkfee dksyfpsipk
        llrelvpqdl irqvspddwk 2041    rsivayfnkh agkskeeakl aflklifkwp tfgsaffeqt
        tepnfpeill iainkygvsl 2101    idpktkdilt thpftkisnw ssgntyfhit ignlvrgskl
        lcetslgykm ddlltsyisq 2161    mltamskqrg srsgk
```

Promoter and Regulatory Sequences

Promoter sequences may also contain additional sequences, for example, those with which it is naturally associated as part of an enhancer, or other sequences. The level of expression of MYO7A may be modulated by manipulating and/or substituting all or a portion of the enhancer/promoter region. For example, different domains within a promoter region may possess different gene regulatory activities. The roles of these different regions are typically assessed using vector constructs having different variants of the promoter with specific regions deleted (that is, deletion analysis). This approach may be used to identify, for example, the smallest region capable of conferring transcriptional control and/or tissue specificity.

Promoters may be strong promoters such as viral promoters. For example, strong viral promoters include the cytomegalovirus (CMV) promoter, the SV40 promoter, the rous sarcoma virus (RSV) promoter and murine leukemia virus (MLV) promoters.

It may be desirable to reduce basal transcription by using a promoter that lacks one or more of the transcriptional regulatory sequences normally associated with the TATA box or initiator sequence of the promoter. For example the promoter may lack a CAAT box motif, and/or an Sp1 consensus binding site, such as is normally found within the SV40 promoter. It may also be possible to use a minimal promoter consisting essentially of a TATA box.

Promoters may comprise additional regulatory control sequences. For example, additional levels of transcriptional control may be used to ensure that expression is confined or selective to certain cell types or under certain conditions. Thus additional enhancers may be operably linked to the polynucleotide encoding MYO7A, either downstream, upstream or both.

The additional regulatory sequence may be a sequence found in eukaryotic genes. For example, it may be a sequence derived from the genome of a cell in which expression is to occur. Additional regulatory sequences may function to confer ubiquitous expression or alternatively tissue-specific expression. Additional regulatory sequences may be preferentially active in one or more specific cell types, e.g., retinal pigment epithelial (RPE) and/or photoreceptor cells.

The term "tissue specific" means a regulatory control sequence which is not necessarily restricted in activity to a single tissue type but which nevertheless shows selectivity in that it may be active in one group of tissues and less active or silent in another group.

Tissue-specific promoters modulating or controlling MYO7A expression may be RPE-specific promoters and/or photoreceptor-specific promoters.

An example of a tissue specific promoter is the VMD2 promoter which is capable of directing retinal pigment epithelium (RPE)-specific expression of an NOI (Esumi et al. (2004) J. Biol. Chem. 279(18):19064-73).

A number of tissue specific enhancers and promoters, for example as described above, may be particularly advantageous in practicing the present invention. In most instances, these enhancers may be isolated as convenient restriction digestion fragments suitable for cloning in a selected vector. Alternatively, enhancer or promoter fragments may be isolated using the polymerase chain reaction. Cloning of the amplified fragments may be facilitated by incorporating restriction sites at the 5' end of the primers. Enhancer fragments may also be synthesized using, for example, solid-phase technology.

Promoters or additional regulatory sequences may also comprise elements that respond to specific stimuli, for example elements that bind steroid hormone receptors. Such regulatory elements that may be inducible, for example such that expression can be regulated by administration of exogenous substances. In this way, levels of expression may be regulated during the life-time of the cell. Inducible means that the levels of expression obtained using the promoter can be regulated. For example, regulatory sequences responsive to the tet repressor/VP16 transcriptional activator fusion protein have been reported (Gossen and Bujard (1992) PNAS USA 89(12):5547-51; Gossen et al. (1995) Science 268(5218): 176-9). A second polynucleotide would typically comprise a strong promoter (e.g. the CMV IE promoter) driving the expression of the tet repressor/VP16 fusion protein. Thus in this example expression would depend on the presence or absence of tetracycline.

Gene Therapy Vehicles

In one aspect, the invention provides constructs or expression vehicles, e.g., expression cassettes, vectors, viruses, and the like, comprising a MYO7A-expressing sequence, e.g., a MYO7A-expressing message RNA or a MYO7A gene, for use as ex vivo or in vitro gene therapy vehicles, or for expression of MYO7A and MYO7A in a cell, tissue or organ for research, drug discovery or transplantation.

In one aspect, an expression vehicle used to practice the invention can comprise a promoter operably linked to a nucleic acid encoding a MYO7A protein (or functional subsequence thereof).

In one aspect, an expression vehicle used to practice the invention is designed to deliver a MYO7A-expressing sequence, e.g., a MYO7A gene or any functional portion thereof to a cell, tissue, organ or individual.

Expression vehicles, e.g., vectors, used to practice the invention can be non-viral or viral vectors or combinations thereof. The invention can use any viral vector or viral delivery system known in the art, e.g., adenoviral vectors, adeno-associated viral (AAV) vectors, herpes viral vectors (e.g., herpes simplex virus (HSV)-based vectors), retroviral vectors, lentiviral vectors and baculoviral vectors.

In one aspect of the invention, an expression vehicle, e.g., a vector or a virus, is capable of accommodating a full-length MYO7A gene or a message, e.g., a cDNA, which for humans is a cDNA about 7 Kb in length. In one aspect, the invention provides a retroviral, e.g., a lentiviral, vector capable of delivering the nucleotide sequence encoding full-length human MYO7A and/or MYO7A in vitro, ex vivo and/or in vivo.

In one embodiment, the invention provides a lentiviral vector that is a third generation lentiviral vector. For example, the lentiviral vector can be a "minimal" lentiviral production system lacking one or more viral accessory (or auxiliary) gene. Exemplary lentiviral vectors for use in the invention can have enhanced safety profiles in that they are replication defective and self-inactivating (SIN) lentiviral vectors. Lentiviral vectors and production systems that can be used to practice this invention include e.g., those described in U.S. Pat. Nos. 6,277,633; 6,312,682; 6,312,683; 6,521,457; 6,669,936; 6,924,123; 7,056,699; and 7,198,784; any combination of these are exemplary vectors that can be employed in the practice of the invention. In an alternative embodiment, non-integrating lentiviral vectors can be employed in the practice of the invention. For example, non-integrating lentiviral vectors and production systems that can be employed in the practice of the invention include those described in U.S. Pat. No. 6,808,923.

The expression vehicle can be designed from any vehicle known in the art, e.g., a recombinant adeno-associated viral vector as described, e.g., in U.S. Pat. App. Pub. No. 2002/0194630, Manning, et al.; or a lentiviral gene therapy vector, e.g., as described by e.g., Dull et al. (1998) J. Virol. 72:8463-8471; or a viral vector particle, e.g., a modified retrovirus having a modified proviral RNA genome, as described, e.g., in U.S. Pat. App. Pub. No. 2003/0003582; or an adeno-associated viral vector as described e.g., in U.S. Pat. No. 6,943,153, describing recombinant adeno-associated viral vectors for use in the eye; or a retroviral or a lentiviral vector as described in U.S. Pat. Nos. 7,198,950; 7,160,727; 7,122,181 (describing using a retrovirus to inhibit intraocular neovascularization in an individual having an age-related macular degeneration); or U.S. Pat. No. 6,555,107.

Any viral vector can be used to practice this invention, and the concept of using viral vectors for gene therapy is well known; see e.g., Verma and Somia (1997) Nature 389:239-242; and Coffin et al. ("Retroviruses" 1997 Cold Spring Harbor Laboratory Press Eds: J M Coffin, S M Hughes, H E Varmus pp 758-763) having a detailed list of retroviruses. Any lentiviruses belonging to the retrovirus family can be used for infecting both dividing and non-dividing cells with a MYO7A-encoding nucleic acid, see e.g., Lewis et al. (1992) EMBO J. 3053-3058.

Viruses from lentivirus groups from "primate" and/or "non-primate" can be used; e.g., any primate lentivirus can be used, including the human immunodeficiency virus (HIV), the causative agent of human acquired immunodeficiency syndrome (AIDS), and the simian immunodeficiency virus (SIV); or a non-primate lentiviral group member, e.g., including "slow viruses" such as a visna/maedi virus (VMV), as well as the related caprine arthritis-encephalitis virus (CAEV), equine infectious anemia virus (EIAV) and/or a feline immunodeficiency virus (FIV) or a bovine immunodeficiency virus (BIV).

Details on the genomic structure of some lentiviruses may be found in the art; e.g., details on HIV and EIAV may be found from the NCBI Genbank database, e.g., Genome Accession Nos. AF033819 (HIV) and AF033820 (EIAV). In alternative embodiments, the lentiviral vector of the invention is an HIV-based lentiviral vector or an EIAV-based lentiviral vector.

In alternative embodiments, lentiviral vectors used to practice this invention are pseudotyped lentiviral vectors. In one aspect, pseudotyping used to practice this invention incorporates in at least a part of, or substituting a part of, or replacing all of, an env gene of a viral genome with a heterologous env gene, for example an env gene from another virus. Pseudotyping examples may be found in e.g., WO 99/61639, WO 98/05759, WO 98/05754, WO 97/17457, WO 96/09400, WO 91/00047 and Mebatsion et al. (1997) Cell 90:841-847. In alternative embodiments, the lentiviral vector of the invention is pseudotyped with VSV.G. In an alternative embodiment, the lentiviral vector of the invention is pseudotyped with Rabies.G.

Lentiviral vectors used to practice this invention may be codon optimized for enhanced safety purposes. Codon optimization has previously been described in e.g., WO 99/41397. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available. Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms. Codon optimization has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimization also overcomes the Rev/RRE requirement for export, rendering optimized sequences Rev independent. Codon optimization also reduces homologous recombination between different constructs within the vector system (for example between the regions of overlap in the gag-pol and env open reading frames). The overall effect of codon optimization is therefore a notable increase in viral titer and improved safety. The strategy for codon optimized gag-pol sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

Vectors, recombinant viruses, and other expression systems used to practice this invention can comprise any nucleic acid which can infect, transfect, transiently or permanently transduce a cell. In one aspect, a vector used to practice this invention can be a naked nucleic acid, or a nucleic acid complexed with protein or lipid. In one aspect, a vector used to practice this invention comprises viral or bacterial nucleic acids and/or proteins, and/or membranes (e.g., a cell membrane, a viral lipid envelope, etc.). In one aspect, expression systems used to practice this invention comprise replicons (e.g., RNA replicons, bacteriophages) to which fragments of DNA may be attached and become replicated. In one aspect, expression systems used to practice this invention include, but are not limited to RNA, autonomous self-replicating circular or linear DNA or RNA (e.g., plasmids, viruses, and the like, see, e.g., U.S. Pat. No. 5,217,879), and include both the expression and non-expression plasmids.

In one aspect, a recombinant microorganism or cell culture used to practice this invention can comprise an expression vector including both (or either) extra-chromosomal circular and/or linear nucleic acid (DNA or RNA) that has been incorporated into the host chromosome(s). In one aspect, where a vector is being maintained by a host cell, the vector may either be stably replicated by the cells during mitosis as an autonomous structure, or is incorporated within the host's genome.

In one aspect, an expression system used to practice this invention can comprise any plasmid, which are commercially available, publicly available on an unrestricted basis, or can be constructed from available plasmids in accord with published procedures. Plasmids that can be used to practice this invention are well known in the art.

In another aspect, constructs of the invention (e.g., a promoter of the invention operably linked to a heterologous MYO7A-encoding sequence) are inserted into the genome of a host cell by e.g., a vector. A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

In alternative aspects, a vector used to make or practice the invention can be chosen from any number of suitable vectors known to those skilled in the art, including cosmids, YACs (Yeast Artificial Chromosomes), megaYACS, BACs (Bacterial Artificial Chromosomes), PACs (P1 Artificial Chromosome), MACs (Mammalian Artificial Chromosomes), a whole chromosome, or a small whole genome. The vector also can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook. Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEMI (Promega Biotec, Madison, Wis., USA) pQE70, pQE60, pQE-9 (Qiagen), pD10, psiX174 pBluescript 11 KS, pNII8A, pN1-116a. pN1118A, pNI-146A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

Gene Therapy Formulations

In one aspect, the invention provides formulations comprising expression vehicles (expression constructs), e.g., vectors, plasmids or recombinant viruses, used to practice the invention; e.g., for ex vivo or in vivo gene therapy to deliver a MYO7A-encoding nucleic acid.

The invention can incorporate use of any non-viral delivery or non-viral vector systems are known in the art and include but are not limited to lipid mediated transfection, liposomes, immunoliposomes, lipofectin, cationic facial amphiphiles (CFAs) and combinations thereof.

In one aspect, expression vehicles, e.g., vectors or recombinant viruses, used to practice the invention are injected intraocularly, e.g., into the retina of an eye. In one aspect, the MYO7A-encoding nucleic acid is administered to the individual intraocularly by subretinal injection. Thus, in one embodiment, the invention provides sterile intraocular injectable formulations comprising expression vehicles, e.g., vectors or recombinant viruses, used to practice the invention.

The invention can incorporate use of any route of administration, e.g., in one embodiment, incorporating routes of administration where the expression construct contacts an appropriate ocular cell. The expression constructs used to practice this invention can be appropriately formulated and administered in the form of an injection, eye lotion, ointment, implant and the like. The expression constructs used to practice this invention can be applied, for example, systemically, topically, subconjunctivally, intraocularly, retrobulbarly, periocularly, subretinally, or suprachoroidally.

In alternative embodiments, it may be appropriate to administer multiple applications and employ multiple routes, e.g., subretinal and intra-vitreous, to ensure sufficient exposure of ocular cells to the expression construct. Multiple applications of the expression construct may also be required to achieve the desired effect.

In one aspect, the MYO7A-encoding nucleic acid-comprising expression construct or vehicle is formulated at a titer of about at least $10^{10}$, $10^{11}$, $10^{12}$, $10^{13}$, $10^{14}$, $10^{15}$, $10^{16}$, or $10^{17}$ physical particles per milliliter. In one aspect, the MYO7A-encoding nucleic acid is administered in about 10, 20, 30, 40, 50, 60, 70, 80, 90, 100, 110, 120, 130, 140 or 150 or more microliter (μl) injections.

Doses and dosage regimens can be determined by conventional range-finding techniques known to those of ordinary skill in the art. For example, in alternative embodiments, about $10^6$, $10^7$, $10^8$, $10^9$, $10^{10}$, $10^{11}$, $10^{12}$, $10^{13}$, $10^{14}$, $10^{15}$, $10^{16}$ or $10^{17}$ viral (e.g., lentiviral) particles are delivered to the individual (e.g., a human patient) in one or multiple doses.

In other embodiments, an intraocular administration comprises from about 0.1 μl to 1.0 μl, 10 μl or to about 100 μl of a pharmaceutical composition of the invention per eye. Alternatively, dosage ranges from about 0.5 ng or 1.0 ng to about 10 μg, 100 μg to 1000 μg of MYO7A-expressing nucleic acid is administered (either the amount in an expression construct, or as in one embodiment, naked DNA is injected). Any necessary variations in dosages and routes of administration can be determined by the ordinarily skilled artisan using routine techniques known in the art.

In alternative embodiments, MYO7A-encoding nucleic acid-comprising expression constructs or vehicles, including the formulations of the invention, are delivered using patches, corneal shields (see, e.g., U.S. Pat. No. 5,185,152), ophthalmic solutions (see, e.g., U.S. Pat. No. 5,710,182), ointments, eye drops and the like. In one embodiment, the MYO7A-encoding nucleic acid-comprising expression constructs or vehicles, including the formulations of the invention, are administered non-invasively using a needleless injection device, e.g., using a BIOINJECTOR 2000™ Needle-Free Injection Management System™ (Bioject, Inc.).

In alternative embodiments, MYO7A-encoding nucleic acid-comprising expression constructs or vehicles, including the formulations of the invention, are delivered using a subretinal injection, using, e.g., a transscleral transchoroidal approach, see, for example, Bennett (1997) Invest. Opthalmol. Vis. Sci. 35:2535; Bennett (1997) Invest. Opthalmol. Vis. Sci. 38:2857.

In some embodiments, the MYO7A-encoding nucleic acid-comprising expression constructs or vehicles, including the formulations of the invention, are administered in multiple doses, e.g., as two or more doses. Different dosages or formulations, or number of administrations, can be administered to at least one eye (e.g., one or both eyes), depending on the clinical effect of the treatment regimen. For example, in one aspect, an ocular cell is contacted with two or more applications of expression constructs or vehicles within about one week, two weeks, three weeks or one month or 90 days or more; or two or more applications are administered to ocular cells of the same eye within about one week, two weeks, three weeks or one month or 90 days or more; or, one, two, three, four, five, or six or more doses can be administered in any time frame (e.g., 2, 7, 10, 14, 21, 28, 35, 42, 49, 56, 63, 70, 77, 85 or more days between doses) so long as gene expression occurs and clinical effects are seen, e.g., blindness is ameliorated.

In one embodiment, the MYO7A-encoding nucleic acid-comprising expression constructs or vehicles, including the formulations of the invention, are administered using an ocular sponge, meshwork, mechanical reservoir and/or mechanical implant. In one embodiment, the MYO7A-encoding nucleic acid-comprising expression constructs or vehicles, including the formulations of the invention, are administered using implants, see, e.g., U.S. Pat. Nos. 5,443,505, 4,853,224 and 4,997,652; or devices as described in U.S. Pat. Nos. 5,554,187, 4,863,457, 5,098,443 and 5,725,493. In one embodiment, the MYO7A-encoding nucleic acid-comprising expression constructs or vehicles, including the formulations of the invention, are administered using an implantable device, e.g., a mechanical reservoir, an intraocular device or an extraocular device with an intraocular conduit, or an implant or a device comprising a polymeric composition for ocular administration. In one embodiment, the MYO7A-encoding nucleic acid-comprising expression constructs or vehicles, including the formulations of the invention, are administered in the form of sustained-release formulations, see, e.g., U.S. Pat. No. 5,378,475, and can comprise gelatin, chondroitin sulfate, a polyphosphoester, such as bis-2-hydroxyethyl-terephthalate (BHET) or a polylactic-glycolic acid.

In one embodiment, the MYO7A-encoding nucleic acid-comprising expression constructs or vehicles, including the formulations of the invention, are administered using invasive procedures, e.g., intravitreal injection or subretinal injection, which optionally can be preceded by a vitrectomy. Subretinal injections can be administered to different compartments of the eye, e.g., the anterior chamber.

In alternative embodiments, injectable compositions comprising the MYO7A-encoding nucleic acid-comprising expression constructs or vehicles, including the formulations of the invention, are administered intramuscularly, intravenously, and intraperitoneally. Pharmaceutically acceptable carriers for injectable compositions are well-known to those of ordinary skill in the art; see Pharmaceutics and Pharmacy Practice, J. B. Lippincott Co., Philadelphia, Pa. Banker and Chalmers, eds., pages 238-250 (1982), and ASHP Handbook on Injectable Drugs, Toissel, 4th Ed., pgs 622-630 (1986).

In alternative embodiments, the MYO7A-encoding nucleic acid-comprising expression constructs or vehicles, including the formulations of the invention, are administered in vivo by particle bombardment, e.g., a gene gun.

In alternative embodiments, the MYO7A-encoding nucleic acid-comprising expression constructs or vehicles, including the formulations of the invention, are administered via an opthalmologic instrument for delivery to a specific region of an eye. Use of a specialized opthalmologic instrument ensures precise administration of the expression vector while minimizing damage to adjacent ocular tissue. Delivery of the expression vector to a specific region of the eye also limits exposure of unaffected cells to reducing the risk of side effects. An exemplary opthalmologic instrument is a combination of forceps and subretinal needle or sharp bent cannula.

Cells and Tissues

The invention also provides cells and tissues for use in gene therapy or drug screening, e.g., cells or tissues harvested from a transgenic animal of the invention, comprising a nucleic acid construct of the invention having a MYO7A-encoding nucleic acid; in one aspect, comprising the human MYO7A gene. Animal cells comprising a nucleic acid construct used to practice this invention include non-human and human mammalian cells. Exemplary animal cells of the invention include CI-10, COS or Bowes melanoma or any mouse or human cell line. The selection of an appropriate host is within the abilities of those skilled in the art.

In one aspect, host cells are cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means; e.g., temperature shill or chemical induction.

Human Retinitis Pigmentosa

The compositions and methods of this invention, including the gene therapy reagents of the invention, can be used for the prevention and/or amelioration (e.g., treatment) of human retinitis pigmentosa (RP). RP is a group of inherited disorders in which abnormalities of the photoreceptors (rods and cones) or the retinal pigment epithelium (RPE) of the retina lead to progressive visual loss. Affected individuals first experience defective dark adaptation or nyctalopia (night blindness), followed by constriction of the peripheral visual field and, eventually, loss of central vision late in the course of the disease.

Drug Discovery

The methods and compositions of the invention can be used in drug discovery. The methods and compositions of the invention can be used for target validation; and, in some applications, can provide a physiologically accurate and less expensive approach to screen potential drugs. Expression arrays can be used to determine the expression of transgenic genes or genes other than a targeted gene or pathway.

Kits and Libraries

The invention provides kits comprising compositions and methods of the invention, including cells, target sequences, transfecting agents, transducing agents, instructions (regarding the methods of the invention), or any combination thereof. As such, kits, cells, vectors and the like are provided herein.

The invention will be further described with reference to the following examples; however, it is to be understood that the invention is not limited to such examples.

EXAMPLES

Example 1

The following example demonstrates that the compositions and methods of this invention can be effective in the amelioration, prevention and/or treatment of conditions or diseases caused by (or exacerbated by) lack of (or diminished) expression of MYO7A in the retina.

In particular, this example demonstrates that MYO7A cDNA can be delivered to retinas in vivo; a predictive animal model using cultured primary RPE cells of Myo7a-null mice, using a lentiviral vector was used. Using a promoter containing elements of the native MYO7A promoter, appropriate levels of myosin VIIa were obtained in the RPE cells, correction of mutant phenotypes—melanosome motility and phagosome digestion in cultured RPE cells, and melanosome localization and opsin clearance from the connecting cilium in vivo—was achieved.

In this study we tested the efficacy of lentiviral mediated MYO7A expression in rescuing mutant phenotypes in the Myo7a-null mice. We demonstrate that current lentiviral vectors can accommodate the large MYO7A cDNA and results in correction of cellular defects in vitro and in vivo, and thus provide a strategy for the retinal therapy of Usher 1B.

Lentiviral-MYO7A Expression

We constructed three HIV-1 derived lentiviral vectors to express human MYO7A protein. The three HIV-1 derived lentiviral vectors had the same third generation/self-inactivating backbone (see, e.g., refs. [36,37]), but differed according to the promoter included to drive expression of full length MYO7A cDNA (see FIG. 1).

The pLV-MYO7A(A) vector contained the 530-bp cytomegalovirus (CMV) promoter. The pLV-MYO7A (B) encoded a chimeric promoter containing 290 bp of the 5' end of the CMV promoter fused to 160 bp of the human MYO7A gene sequence that spans the boundary of the first intron and the second exon. The pLV-MYO7A (C) included only the 160-bp MYO7A sequence. These lentiviral vectors were used to produce viruses pseudotyped with the glycoprotein of vesicular stomatitis virus (VSV.G) (see, e.g., refs. [38,39]) Anti-MYO7A labeling of infected HEK 293T cells showed robust expression by LV-MYO7A(A), weak expression by LV-MYO7A(B), and no detectable expression by LV-MYO7A (C) (see FIG. 6a-d).

Figure 6:
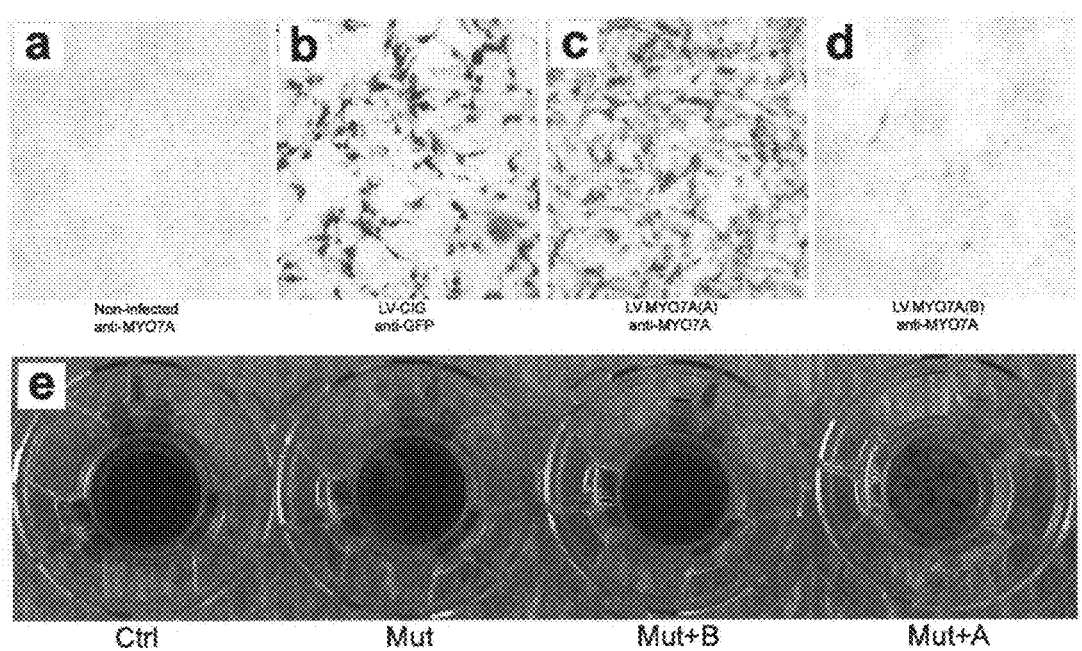
FIGS. 6a-d show lentivirus-mediated transgene expression and promoter activities in HEK 293T cells. Human embryonic kidney 293T cells were infected by various lentiviruses for 48 hrs. Transgene expression was detected by immunolabeling GFP (b) or MYO7A (a, c, d). Note that HEK293T cells infected by LV-MYO7A(A) and LV-CIG viruses, encoding the CMV promoter, show robust expression of MYO7A and GFP, respectively. In contrast, HEK 293T cells, infected by LV-MYO7A(B) which carries the CMV-MYO7A chimeric promoter, show poor expression. (e) Photographs of cultures illustrate RPE cell densities from Myo7a$^{+/-}$ (ctrl), Myo7a$^{-/-}$ (Mut) and Myo7a$^{-/-}$ infected with LV-MYO7A(B) (Mut+B)

We next examined lentiviral mediated MYO7A expression in vitro in primary cultures of RPE cells from Myo7a$^{-/-}$ (MYO7A-null mutant) shaker1 mice. Due to the weak activity of the LV-MYO7A (B) chimeric promoter in the HEK cells, the titer of the LV-MYO7A (B) virus was determined by MYO7A immunostaining in Myo7a$^{-/-}$ RPE cells, infected by serially diluted viral stocks, and was found to be 1×10$^9$ TU/ml. This titer is comparable to the titer of LV-MYO7A (A) virus obtained through infection of the HEK 293T cells (2×10$^9$ TU/ml). When similar titer LV-MYO7A (A) and LV-MYO7A (B) viruses were used to infect primary Myo7a$^{-/-}$ RPE cells, no MYO7A was detected by 3 days post infection, but, after 5 days, immuno-labeling indicated that more than 95% of the cells were transduced by the two viruses. However, treatment with LV-MYO7A (C) did not yield any detectable expression of MYO7A in RPE cells (data not shown). The LV-MYO7A (B) virus resulted in expression levels and localization of MYO7A that were comparable to that in the Myo7a$^{+/-}$ control cells, as determined by Western blot and immunofluorescence labeling (see FIG. 2a, 2b, 2e). In contrast, infection with the LV-MYO7A(A) resulted in much higher levels of MYO7A expression, such that MYO7A accumulated in large aggregates and cell death was detected after 5 days of infection (see FIG. 2c, 2d; FIG. 6e). These results indicate that the chimeric promoter encoded by LV-MYO7A (B) was able to drive relatively normal levels of MYO7A expression in cultured RPE cells, and the 160-bp MYO7A gene sequence alone was insufficient to drive expression in HEK 293T or RPE cells.

To determine the transduction efficiency of VSV.G packaged lentiviruses in vivo, we performed subretinal injection of Myo7a$^{-/-}$ neonatal mice with LV-MYO7A(A) or a lentivirus expressing EGFP from the CMV promoter (LV-CIG) (see, e.g., ref. [37]). Consistent with results obtained from RPE cell cultures in vitro, lentiviruses with the CMV promoter effectively drove the transgene expression in the RPE cell layer in vivo. However, injection of LV-MYO7A (A) into either neonatal or adult mice caused RPE atrophy within a week. Neither neonatal nor adult subretinal injection of lentiviruses containing the CMV promoter resulted in substantial viral transduction of the neural retina.

Figure 2:
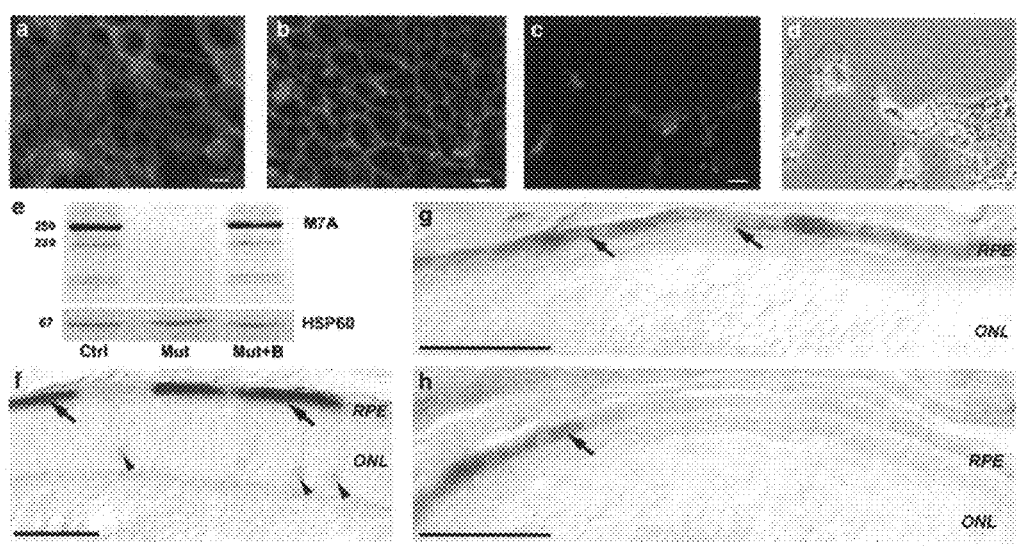
FIGS. 2a-h show lentiviral vector-mediated expression of MYO7A. (a-c) Immunofluorescence shows MYO7A immunolabel in (a) Myo7a$^{+/-}$ RPE, (b) Myo7a$^{-/-}$ RPE, 7 days after infection with LV-MYO7A(B), and (c) Myo7a$^{-/-}$ RPE, 7 days after infection with LV-MYO7A(A). (d) A phase contrast image of panel c. (e) Western blot of MYO7A protein (upper panel) in Myo7a$^{+/-}$ RPE (Ctrl), Myo7a$^{-/-}$ RPE (Mut) and Myo7a$^{-/-}$ RPE, 5 days after infection with LV-MYO7A(B) (Mut+B). HSP60 labeling (lower panel) was used as a loading control. (f) Alkaline phosphatase (AP) histochemistry of a retinal section from an albino control mice. The retina was injected at P4 with LV-AP(B) and fixed at P14. Arrows and arrowheads indicate AP staining in the RPE and photoreceptor cells, respectively. Area shown is away from the site of injection. (g, h) MYO7A immunostaining (arrows) of the RPE in the central (g) and peripheral (h) regions of the retina from an albino Myo7a$^{-/-}$ mouse. The retina was injected centrally at P96 with the LV-MYO7A(B) virus and fixed 6 days later. Faint, non-specific staining, see e.g., ref. [9], is evident in the photoreceptor synaptic layer. RPE, retinal pigment epithelium; ONL, outer nuclear layer. Scale bars=20 μm (a-d), 50 μm (f-h).

To determine the efficiency of transgene expression from lentiviral vectors encoding the CMV-MYO7A chimeric promoter in vivo, we constructed and produced a lentivirus, LV-AP(B), in which the alkaline phosphatase (AP) reporter gene replaced the MYO7A cDNA in LV-MYO7A(B). A viral stock of LV-AP(B) with a titer of 10$^7$ TU/ml was injected sub-retinally at P4. At P14, the majority of injected eyes showed positive AP histochemical staining in the RPE (6 out of 8), and all eyes that showed RPE transduction also contained AP-positive photoreceptor cells. The AP signals in the RPE cells ranged from 70-80% (3/8) to 10-30% (3/8) of the entire RPE layer on cross sections. Moreover, the AP activity as detected by histochemistry indicated that the chimeric promoter resulted in significantly higher expression levels in the RPE than in the photoreceptor cells (FIG. 2f).

Immunocytochemical labeling of neonatal Myo7a$^{-/-}$ retinas, injected with LV-MYO7A(B) virus, showed that 30-50% of the RPE was MYO7A positive, with most of the negative cells located furthest from the injection site. The MYO7A expression level varied from cell to cell (FIG. 2g, 2h). Despite LV-AP(B) transduction of photoreceptor cells, significant MYO7A immunogold labeling could not be detected in these cells, following injection of LV-MYO7A(B).

Together, these results show that lentiviral vectors are capable of expressing the large MYO7A cDNA, and that VSV.G pseudotyped lentiviruses, in conjunction with appropriate promoters, can transduce RPE cells as well as photoreceptor cells.

Correction of Mutant Phenotypes in Primary Cultures of RPE Cells

Since the level of expression of MYO7A by the LV-MYO7A(B) virus in Myo7a$^{-/-}$ RPE cells was similar to that in control cells, we tested whether transduction by this virus could correct previously identified mutant phenotypes.

Myo7a[-/-] RPE cells do not digest ingested rod outer segments (ROSs) as well as control cells, due to retarded transport to the lysosomes in their basal region (see e.g., ref.[18]). In testing for correction of this phenotype, we measured the rate of digestion of ingested ROSs by RPE cells, following a 20-min exposure to ROSs in the medium. ROSs remaining in the RPE cells (and thus defined as undigested) were detected by opsin immunolabeling. Two hours after the exposure to ROSs, there were significantly fewer remaining ROSs in Myo7a[-/-] cells that had been pretreated with LV-MYO7A(B) than in untreated mutant cells (5-10 fold). The number of ROSs was similar to that detected in Myo7a[+/-] control cells (see FIGS. 3a-d).

Figure 3:
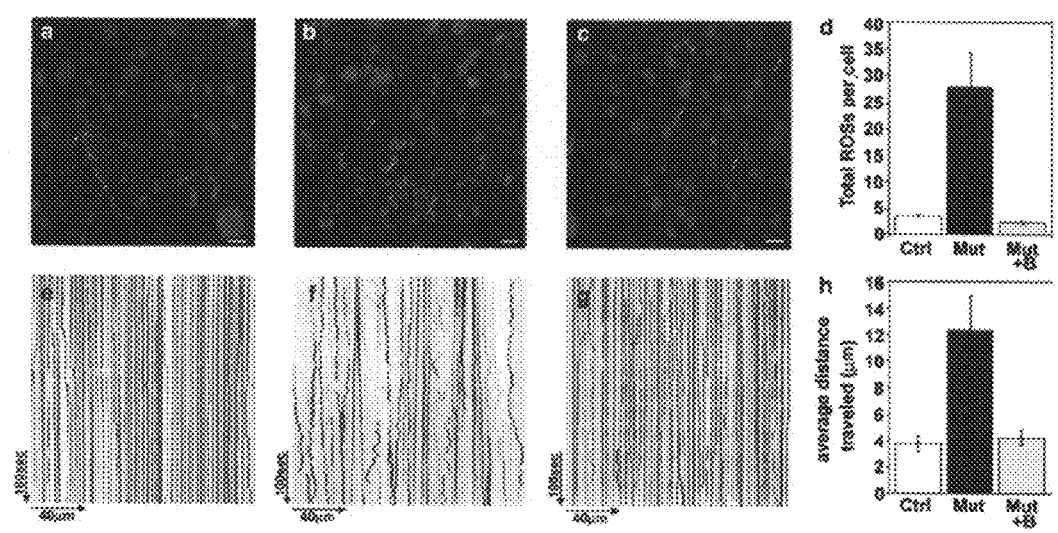
FIGS. 3a-h show lentiviral correction of Myo7a-mutant phenotypes in RPE primary cultures. (a-c) Immunofluorescence of ROSs remaining in Myo7a$^{+/-}$ RPE (a), Myo7a$^{-/-}$ RPE (b) and Myo7a$^{-/-}$ RPE infected with LV-MYO7A(B) (c). The ROSs are represented by green dots from opsin labeling (e.g. arrows). Nuclei are stained blue. (d) Bar graph showing the total number of ROSs per cell in Myo7a$^{+/-}$ RPE (Ctrl), Myo7a$^{-/-}$ RPE (Mut) and Myo7a$^{-/-}$ RPE infected with LV-MYO7A(B) (Mut+B). (e, f, g) Kymographs (showing distance traveled in relation to time) illustrate the differences in movements of individual melanosomes from Myo7a$^{+/-}$ RPE (e), Myo7a$^{-/-}$ RPE (f), and Myo7a$^{-/-}$ RPE infected with LV-MYO7A(B) (g). The more constrained movements of melanosomes in control and corrected RPE are evident by less displacement. Each line represents the movement of an individual melanosome. (h) Bar graph showing the average distance per 5 min, traveled by randomly selected individual melanosomes measured from Myo7a$^{+/-}$ RPE (Ctrl), Myo7a$^{-/-}$ RPE (Mut) and Myo7a$^{-/-}$ RPE infected with LV-MYO7A(B) (Mut+B). Scale bars (a-c)=20 μm. Error bars in d and h represent +/−s.e.m.

In Myo7a[-/-] RPE cells, melanosomes undergo rapid movements over much longer ranges than they do in control RPE cells (see e.g., ref.[11]). Thus, we tested whether treatment with LV-MYO7A (B) could correct this defect in melanosome motility. To monitor the movements of melanosomes, time-lapse imaging of live cells and particle tracking was used to record the displacement of individual melanosomes. FIGS. 3e-g illustrates a series of resulting kymographs from different melanosomes. In control cells (FIG. 3e) the majority of individual melanosome traces showed little or no displacement over time and thus appear largely as smooth vertical lines, with only a few small sloping regions. In contrast, melanosome traces from mutant cells (FIG. 3f) showed much larger and more frequent displacements (sloped regions) over time. Mutant cells treated with LV-MYO7A (B) (FIG. 3g) had melanosome traces comparable to control cells. A quantitative analysis of these melanosome tracks confirmed that the long range movements of melanosomes found in the mutant cells were absent in treated cells; melanosome movements became restricted as in control cells (FIG. 3h).

Therefore, lentiviral vector-mediated MYO7A expression effectively corrected two mutant phenotypes, defective phagocytosis and abnormal melanosome motility, found in Myo7a[-/-] RPE cells.

Correction of Melanosome Mislocalization in Myo7a-Null Mice In Vivo

Figure 4:
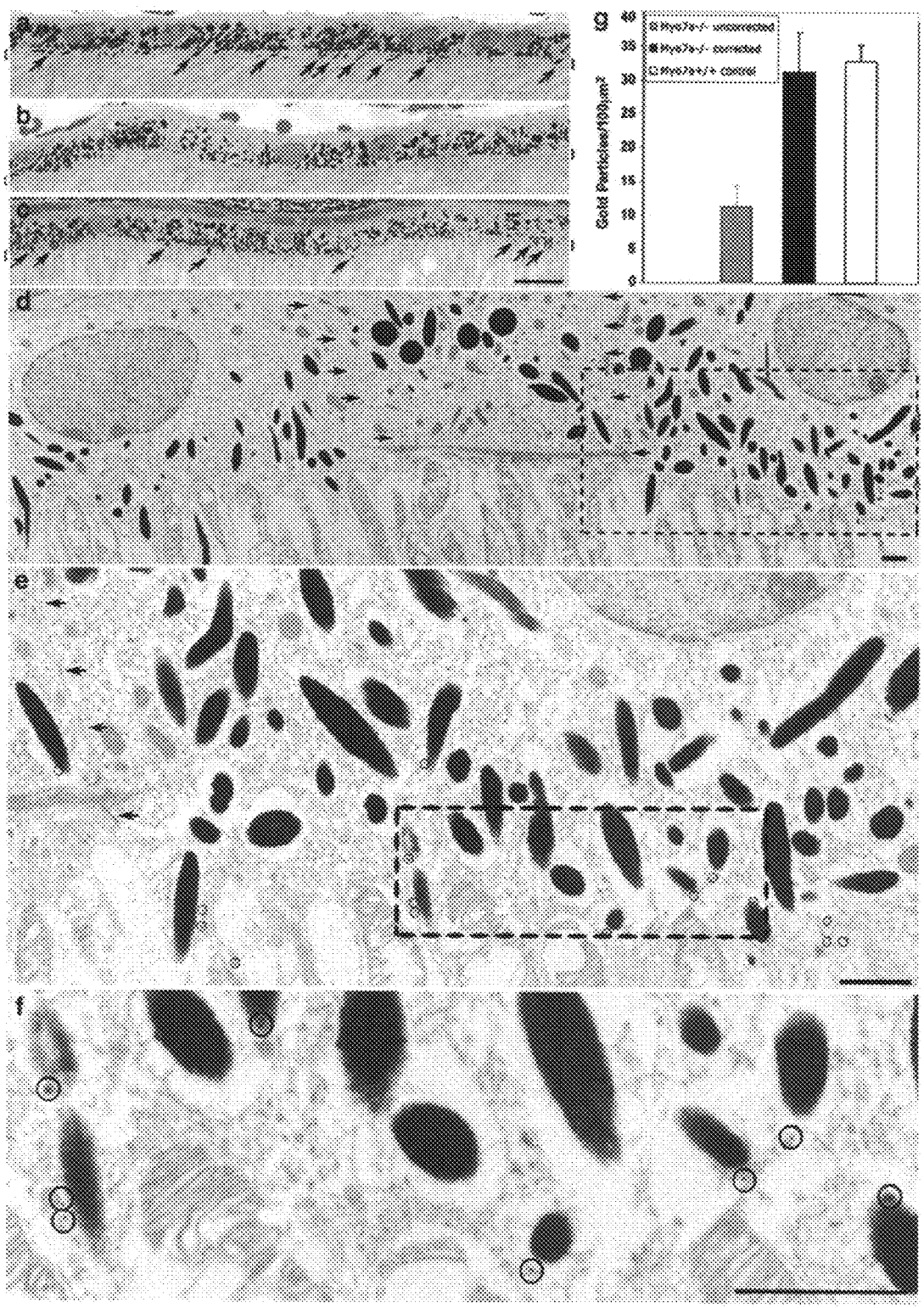
FIGS. 4a-g show correction of melanosome localization in the RPE in vivo. Semithin (a-c) and ultrathin (d-f) LR White sections of (a) a Myo7a$^{+/+}$ retina, (b) a Myo7a$^{-/-}$ retina, and (c-f) a Myo7a$^{-/-}$ retina, infected with LV-MYO7A(B) at P1 and analyzed at P16. In a-c, brackets indicate the RPE apical processes. Arrows indicate some of the melanosomes localized in the RPE apical processes. Arrows in d and e indicate the RPE cell boundaries. Note that the central RPE cell in the field does not contain any melanosomes in the apical region, whereas the two flanking cells do. The section has been immunogold-labeled for MYO7A. Boxed areas in (d) and (e) were enlarged in (e) and (f) respectively, to show immunogold particles (all have been circled). The cytoskeleton of the zonula adherens is evident in (d) across the entire profile of the central cell (bottom right arrow), indicating that the section is near the periphery of the cell. The lack of melanosomes evident in the apical RPE is not due to the plane of the section. In control RPE, melanosomes are obvious in the apical processes of cells sectioned in this manner. Scale bars: a-c, 10 μm; d-f, 1 μm. Bar graph (g) shows the relationship between the density of MYO7A immunogold particles and the observed correction of melanosome localization (data for each bar were obtained from 15-18 cells). Error bars represent +/−s.e.m.
Figure 5:
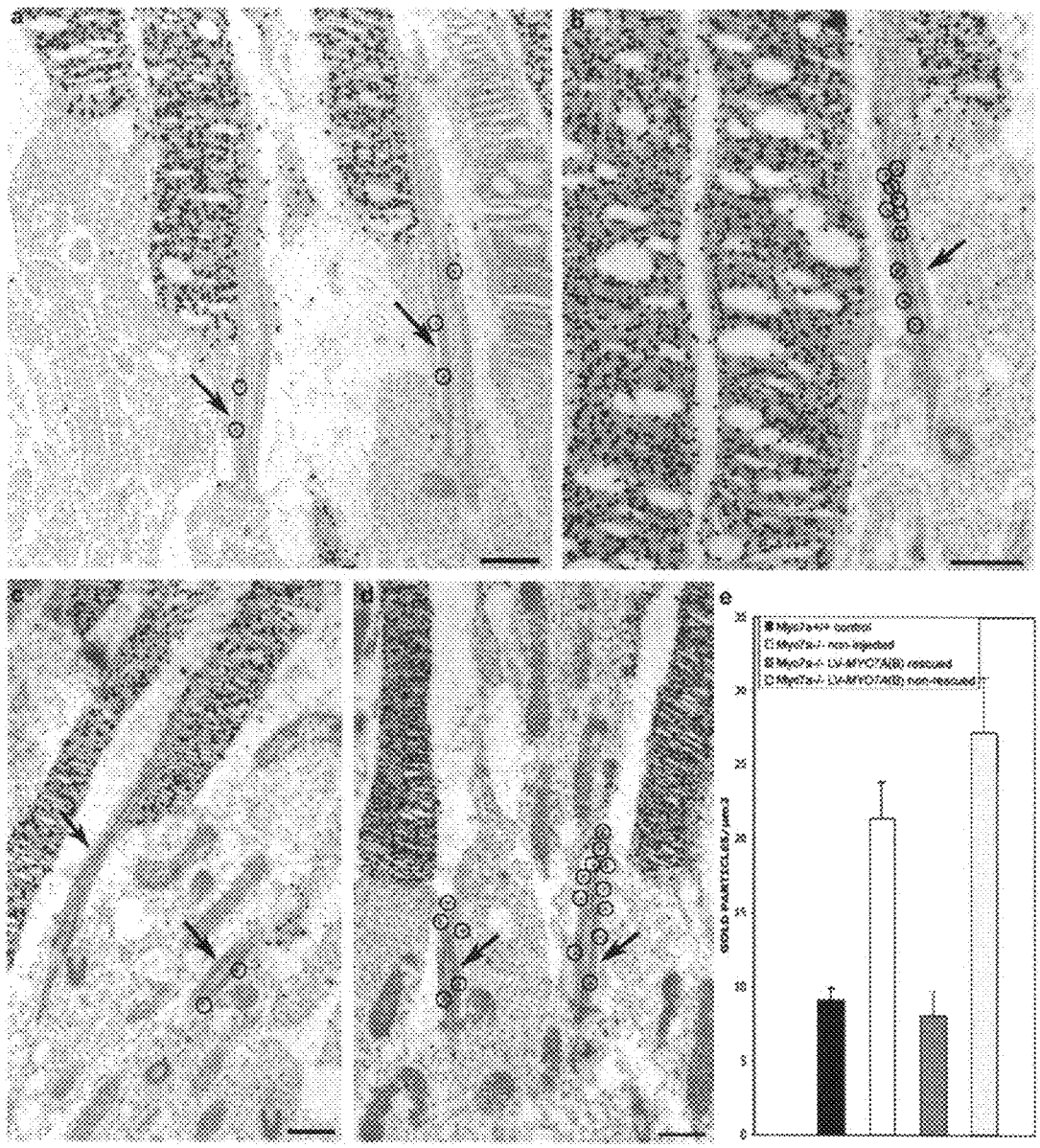
FIGS. 5a-e show correction of opsin distribution in the connecting cilia of photoreceptor cells, following in vivo injection of LV-MYO7A(B). Opsin immunogold labeling of sections of photoreceptors from (a) a Myo7a$^{+/+}$ retina, (b) a Myo7a$^{-/-}$ retina, (c, d) a Myo7a$^{-/-}$ retina, infected with LV-MYO7A(B) at P1 and analyzed at P16. The photoreceptors in c are beneath an RPE cell that had correctly distributed melanosomes. Those in (d) are distant from the injection site, where the RPE melanosomes are all distributed as in MYO7A-null RPE cells. Scale bars: 500 nm. (e) Bar graph showing the concentration of opsin immunogold labeling in the cilia of photoreceptors like those in a-d (n=43, 63, 28, and 17 cells, respectively). Error bars represent +/−s.e.m.

A readily apparent mutant phenotype in shaker1 mouse retinas is the complete absence of melanosomes from the apical regions of the RPE cells (see e.g., ref.[17]). We thus tested for correction of this phenotype following subretinal injection of LV-MYO7A (B). Semithin sections were examined by light microscopy 4 to 19 days after injection. No correction or MYO7A was detected 4 days after injection. By 6 days or later, some, but not all RPE cells contained melanosomes in their apical processes (FIG. 4a-c). More corrected cells were observed near the site of injection, but, even here, some cells that were not corrected were evident.

To correlate the level of MYO7A expression with correction of melanosome distribution, we quantified immunogold label of MYO7A on sections of LV-MYO7A (B)-treated Myo7a[-/-] retinas. The mosaic effect of the correction was also evident by electron microscopy, with corrected RPE cells neighboring uncorrected cells, based on the presence or absence of apical melanosomes (FIG. 4d). In retinas infected at P1 and analyzed at P16, 94% of the cells, within 1.0 mm of the injection site, contained above background labeling, indicating they had at least been infected. Of these cells, 55% had corrected melanosome distribution. These corrected cells had a mean concentration of gold labeling that was comparable to Myo7a[+/+] retinas, whereas the uncorrected cells (those that had been transduced but expressed lower levels of the transgene) had a mean concentration that was 65% lower than the wild type level (FIGS. 4e-g). These results demonstrate that correction of the normal melanosome distribution in vivo was correlated with LV-MYO7A (B)-mediated MYO7A expression. Moreover, it is evident that a threshold level of MYO7A is necessary for correction.

Correction of Opsin Accumulation in the Photoreceptor Cilia of Myo7a-Null Mice

Myo7a-null mice were found to have a 2.6-fold higher concentration of opsin immunoreactivity in the connecting cilia of their photoreceptor cells (see e.g., ref.[23]). To test if this mutant phenotype had been corrected, we immunogold-labeled EM sections with opsin antibodies and counted the gold particles in the connecting cilia of photoreceptors underlying corrected RPE cells (i.e., cells containing apical melanosomes). For negative and positive controls, we also quantified opsin labeling in the connecting cilia of photoreceptors distant from the site of injection, where no correction of melanosome distribution was evident, as well as photoreceptors in control and untreated mutant retinas. Connecting cilia of photoreceptor cells associated with corrected RPE cells showed, on average, normal opsin labeling, indicating correction (FIGS. 5a-e).

Discussion

These data demonstrate the efficacy of the compositions and methods of this invention in lentiviral gene therapy in an art-accepted mouse model for the recessive combined deafness and blindness syndrome, Usher 1B. We demonstrated that recombinant lentivirus-mediated expression of the human MYO7A cDNA leads to effective rescue of several mutant phenotypes in Myo7a-null RPE and photoreceptor cells in vitro and in vivo. The correction of cellular abnormalities in the RPE seems to be relative to the expression level of MYO7A protein. These findings demonstrate the therapeutic potential of lentiviral vectors for the retinal dystrophy of Usher 1B.

Expression of a Large Gene by a Lentiviral Vector

The most successful and widely-used viral vector for retinal gene therapy has been recombinant AAV. However, its carrying capacity is limited to 5.2 Kb (see e.g., ref.[40]). Here, we chose the third generation, recombinant lentiviral vector, in large part because of its high packaging capacity (see e.g., refs.[36,35]). Our results show that the current lentiviral vector can accommodate the 6962-bp human MYO7A cDNA plus at least 600 bp of promoter sequence. Furthermore, protein and functional analyses indicate that the lentiviral vector produced MYO7A of the expected molecular weight and cellular activity. To our knowledge, this is the largest transgene expressed by a viral vector in the RPE, or elsewhere in the retina. Our results thus further establish (demonstrate) the effectiveness of a lentiviral-based gene transfer approach in treating retinal and other inherited diseases caused by loss of function of large genes.

LV-MYO7A Expression and Correction of Cellular Events in Photoreceptor and RPE Cells MYO7A is normally present in photoreceptor cells as well as the RPE as detected by immuno-electron microscopy, although the amount in the photoreceptors appears to be only a small fraction of that in the RPE. This difference in expression levels is most evident in immunofluorescence images of rodent retinas, where labeling of the photoreceptor cells is nearly undetectable, despite a very strong signal in the RPE cells, see e.g., refs.[7,41,9]. Most of the MYO7A in the RPE is associated with melanosomes, see e.g., refs.[10,19,11]. Quantitative studies have shown that this proportion (70-80%) is similar among mouse, pig, and human RPE, see e.g., ref.[11]. A major focus of the present study was on RPE cell correction, especially the role of MYO7A in melanosome motility and localization, for which we have the most tractable assays. However, in one aspect of the invention, the treatment of Usher 1B patients encompasses increasing MYO7A expression in both RPE and photoreceptor cells to normal levels.

Previous studies have shown that VSV.G packaged lentiviral vectors can transduce rodent photoreceptor cells when encoding a photoreceptor-specific promoter, see e.g., refs. [42,43]. Our results of LV-AP(B) infection indicate that lentiviral vectors containing the CMV-MYO7A chimeric promoter can drive differential transgene expression in the RPE and photoreceptor cells. The much higher level of expression in the RPE cells resembles the endogenous expression patterns of MYO7A in the mouse retina, and may be a function of the native enhancer element included in the CMV-MYO7A promoter. However, the proportion of photoreceptors that were transduced, as indicated by the AP reporter, is low. There are several factors that might have contributed to this weaker transduction of photoreceptor cells. Firstly, VSV-G packaged viral particles might be preferentially taken up by the RPE. Secondly, the titer of the LV-AP(B) virus used was relatively low ($1 \times 10^7$ TU/ml). Lastly, access of the vector to the photoreceptor cells is likely to have been partly responsible. Gruter et al., showed that removal of the physical barrier around adult photoreceptor cells with neuraminidase greatly increases transduction efficiency, see e.g., ref. [44]. With a view to clinical therapy, it is important to note that the extent of this physical barrier most likely differs between normal and partially-degenerated retinas.

This study demonstrates the importance of transgene expression levels in viral-based gene replacement therapies of the RPE. We found that the level of transgene expression mediated by the lentiviral vector is important for the correction of melanosome mislocation phenotype in vivo. Quantification of immunogold labeling of MYO7A indicated that uncorrected RPE cells that had nevertheless apparently been transduced (since they contained above background levels of MYO7A) possessed an average of 35% of the wild type level of MYO7A. There was a range of expression levels among these cells (note error bar in FIG. 4f), so that the lower threshold level for correction of the melanosome mislocalization phenotype is likely to be substantially higher than 35%.

On the other hand, our data seem to indicate that excessive levels of MYO7A are detrimental to RPE cells in vitro and in vivo; although it remains undetermined whether the cells are more sensitive to high levels of human MYO7A than they would be to comparable levels of murine MYO7A. In any case, it appears that there is a range of MYO7A expression levels, with upper and lower limits, that needs to be achieved in order to effect correction of mutant phenotypes in the RPE.

Despite the unambiguous AP reporter signals in the photoreceptor cells, we did not detect above background levels of MYO7A transgene expression in the photoreceptor cells by immunocytochemistry in virally transduced retinas. Nevertheless, photoreceptor cells, adjacent to corrected RPE cells, had normal, low levels of opsin label in their connecting cilia, indicating that they, too, had been corrected. The photoreceptor cells may have expressed MYO7A at a level that was lower than that found in wild-type cells by immuno-labeling, but still sufficient to effect correction of the opsin distribution (in unpublished observations, we have found that retinas from wild-type (Myo7a$^{+/+}$) mice, rather than the lower-expressing heterozygous (Myo7a$^{+/-}$) mice, are needed for reliable MYO7A labeling of photoreceptor connecting cilia). Alternatively, the phenotype correction might have resulted indirectly from LV-MYO7A expression in the RPE cells. More efficient disposal of phagosomes by the RPE, the end stage of the disk renewal process, might have removed inhibition of earlier stages, and thus corrected opsin transport along the photoreceptor connecting cilium and distal migration of disks along the outer segment. But, given the normal presence of MYO7A in the connecting cilium (see e.g., ref. [12]), a direct effect on the photoreceptor cells seems more likely. The transduction efficiency of the photoreceptor cells by LV-MYO7A should have been much higher than that by LV-AP, since the titer of the LV-MYO7A(B) was 100-fold greater.

The considerable heterogeneity of lentiviral-mediated transgene expression observed among different RPE and photoreceptor cells likely results from variation in transduction efficiency as well as the impact of different integration sites, see e.g., refs. [45,46]. Strategies for providing predictable regulation of the level of transgene expression may be a consideration, especially with a view to the clinical therapy methods of this invention. In alternative embodiments, such strategies might include (1) using chromatin insulators, as described, e.g., in refs. [47,48], to obviate the effects of different integration sites and allow transgene expression to be regulated only by the virally-encoded promoter elements, or (2) simply avoiding integration, by using integrase-deficient lentiviruses, which have been shown to mediate effective, stable transduction of retinal cells, see e.g., ref. [49].

A Treatment for Blindness in Usher 1B

The shaker1 mice have been an important animal model for characterizing cellular defects that potentially exist in humans with mutant MYO7A. Defects in the renewal of photoreceptor disk membranes (as manifest by opsin accumulation in the photoreceptor connecting cilium and retarded phagosome processing) and melanosome trafficking may be central to the development of the disease pathology found in Usher 1B patients, even though the photoreceptor cells of shaker1 mice do not appear to degenerate significantly during the lifespan of the animal (at least on certain backgrounds), see e.g., refs. [15,16]. Lack of photoreceptor cell loss is also found in a number of other mouse models of retinal degeneration, such as the Abca4 knockout mouse, a model for Stargardt macular degeneration, see e.g., ref. [50], and all the known mouse models for the other types of Usher 1, see e.g., refs. [51-53].

With regard to diseases caused by loss of gene function, as appears to occur in Usher 1B, the critical question is how well the introduced gene mimics wild-type function. The most direct assessment of this question is by analysis of gene expression level and cell-based assays, rather than measurements of cell loss. Cell death is a downstream event that can be influenced by many factors—for example, the mere act of subretinal injection can promote photoreceptor survival, see e.g., ref. [54]. Lack of cell death is clearly an important test for the absence of unintended side effects, but such tests can also be performed independent of efficacy studies on any non-mutant species. From a practical viewpoint, rapid responses to treatment are desirable endpoints in any clinical trial. Inhibition of retinal degeneration is unlikely to be a particularly useful measure because of its relatively slow time-course.

In conclusion, we have demonstrated that cellular abnormalities, representing primary responses to lack of MYO7A in RPE and photoreceptor cells, can be corrected by the lentiviral gene therapy methods of this invention. In demonstrating gene therapy as a treatment for Usher 1B blindness using the compositions and methods of this invention, we have also provided an assessment of the levels of MYO7A expression required for the correction of mouse retinal cellular phenotypes. More generally, these results demonstrate the utility of lentiviral vectors in the delivery of large transgenes in gene therapy.

Materials and Methods

Animals

Shaker1 mice carrying the 4626SB allele, an effective null mutation, see e.g., refs. [15,23], were used on either the C57BL6 or BS (albino) genetic backgrounds, and maintained and genotyped as described in refs. [23,18]. They were maintained on a 12-hr light/12-hr dark cycle, with exposure to 10-50 lux of fluorescent lighting during the light phase, and were treated according to NIH, UCLA, and UCSD animal care guidelines. Homozygous mutants were distinguished from the heterozygous controls by their hyperactivity, head-tossing and circling behavior, see e.g., ref. [13], and/or by a PCR/restriction digest assay. CD1 albino mice were also used for testing of the chimeric promoter.

Construction of Lentiviral Vectors

A full-length, human MYO7A cDNA was assembled from three overlapping fragments, pM7-10a, see e.g., ref. [7], and the IMAGE EST clones BE780659 and A1355462, using the pCMV-SPORT6 vector (Invitrogen). The assembled cDNA was confirmed by complete sequencing. The lentiviral backbone used to construct LV-MYO7A viral vectors was derived from a third generation, self-inactivating vector, LV-CIG, see e.g., ref. [37]. The posttranscriptional regulatory element of woodchuck hepatitis virus (WPRE) (see e.g., ref. [55]) was deleted from the LV-CIG vector. A total of 6962 bp of the MYO7A cDNA, including the entire translated region, 275 bp of 5' UTR, and 39 bp of 3' UTR without the polyadenylation site, was used to replace the cre-IRES-EGFP sequence in the LV-CIG vector, see e.g., ref. [37]. For the LV-MYO7A(A) vector, the MYO7A cDNA was under the control of the 530 bp human cytomegalovirus (CMV) promoter. LV-MYO7A(B) encoded a chimeric promoter containing the 5' 290 bp of the CMV promoter and a 160 bp MYO7A genomic sequence (chromosome (Chr.) 11q, nucleotides (nt) 132114-132273 of AP000752, GenBank), which resides immediately upstream of the start codon and overlaps with a partially characterized MYO7A regulatory sequence, see e.g., ref. [56]. LV-MYO7A (C) contained only the 160 bp human MYO7A genomic sequence. The LV-AP(B) contained the same chimeric promoter as LV-MYO7A(B), except that the MYO7A cDNA was replaced by the human placental alkaline phosphatase (AP) cDNA.

Production of Lentiviral Stocks

Human embryonic kidney (HEK) 293T cells were cotransfected with three packaging plasmids, pLP1, pLP2, pLP/VSVG, and a given lentiviral vector construct, using Lipofectamine 2000, as described, e.g., in ref. [36] (Invitrogen, Carlsbad, Calif.). After 24 hrs, culture medium was replaced by fresh 10% FCS/DMEM or the serum-free CD293 (Invitrogen). Virus-containing medium was collected at 48 hrs post transfection, filtered through 0.4 mm Durapore units (Millipore), and concentrated by ultracentrifugation, as described, e.g., in ref. [57]. Viral titers, defined as transducing units per ml (TU/ml), were determined by immunostaining cells infected with serially-diluted viral stocks. In the case of LV-MYO7A (B), which gave very weak transgene expression in HEK293T cells, viral titer was determined by anti-MYO7A immunostaining of infected primary mouse Myo7a$^{-/-}$ RPE cells. The titer of LV-AP(B) was determined by AP histochemistry, see e.g., ref. [58], following infection of ARPE19 cells. Concentrated lentiviral stocks used for in vivo and in vitro studies had titers of $2\times10^8$ TU/ml for LV-CIG 37, $2\times10^9$ TU/ml for LV-MYO7A(A), $1\times10^9$ TU/ml for LV-MYO7A(B), and $1\times10^7$ TU/ml for LV-AP(B).

Lentiviral Infection of Cultured RPE Cells

RPE cells from Myo7a$^{+/-}$ and Myo7a$^{-/-}$ mice were isolated as described previously, see e.g., refs. [18,59]. Concentrated viral stocks were diluted 5-fold in medium containing high glucose DMEM, 10% FCS, 1×MEM non-essential amino acids, 100 U/ml penicillin, 100 mg/ml streptomycin, and 6 μg/ml hexadimethrine bromide (Polybrene; Sigma, St. Louis, Mo.). Isolated cells were seeded in virus-containing medium (50 μl) in the upper well of 24-well transwell filter plates (Corning), and incubated at 37° C. After 3 hrs, 0.5 ml of fresh virus-free growth medium without Polybrene was added to the lower well and the volume in the upper well was increased to 0.1 ml.

Viral Delivery In Vivo

Mice were anesthetized with 2.0-3.0% isoflurane inhalation. The injection needle (32 gauge, Hamilton) was inserted through the temporal limbus and 0.5 μl of viral solution was injected into the ventral subretinal space of neonatal or adult mice. The viral solution consisted of concentrated viral stock with 6 μg/ml polybrene and 0.025% Fast Green dye (Sigma).

Labeling of Cultured RPE Cells and Retinal Cryosections

Cultured cells were fixed and labeled with affinity purified MYO7A antibody, pAb2.2, see e.g., ref. [12], followed by an Alexa Fluor 594 nm secondary antibody (Molecular Probes). For western blots, lysates were obtained from cells cultured on transwell plates for 5 days. After blotting, proteins were labeled using MYO7A pAb2.2 and HSP60 mAb (Stressgen Biotechnologies), and an alkaline phosphatase-conjugated secondary antibody. Thick (14 μm) retinal cryosections were immunolabeled with MYO7A pAb2.2, followed by a biotinylated secondary antibody and horseradish peroxidase (HRP) detection, using the Elite ABC kit (Vector Labs). AP histochemistry was performed as described in ref. [58].

Analyses of Cultured RPE Cells

The digestion of mouse ROSs (rod outer segments) by the RPE cells was assayed as described in ref. [18]. Briefly, 7 days after viral infection, cells were incubated with ROSs for 20 min, washed repeatedly with cold PBS to remove unbound ROSs, and incubated for a further 2 hrs. The total number of ROSs remaining in the cells, and the number of DAPI positive nuclei per field were counted in images recorded from five randomly selected fields of view at 200× magnification. This procedure was repeated on five separate filters per treatment.

Melanosome motility datasets were recorded, using brightfield time-lapse microscopy, from four or five live RPE cells (from different cultures) per treatment, 7 days after viral infection, as described in ref. [11]. Kymograph traces and displacement measurements were extracted for 80-90 melanosomes per treatment using the multiple kymograph function in ImageJ, a public domain, Java-based image processing program developed at the National Institutes of Health, DHHS.

Light Microscopy and Immunoelectron Microscopy of Retinas

Cryosections stained for immunocytochemistry or histochemistry were imaged by DIC optics. Eyecups were processed for embedment in LR White, and semi-thin and ultrathin sections were prepared, as described previously, see e.g., ref. [11]. Ultrathin sections were labeled with affinity-purified MYO7A antibody, followed by a 10-nm gold secondary antibody. Negative control sections processed at the same time included those from Myo7a$^{-/-}$ retinas and those from the same retinas that were incubated with 1 mg/ml of the original antigen fusion protein together with the MYO7A antibody.

MYO7A immunogold density was determined on sections of same-aged Myo7a$^{+/+}$ retinas and Myo7a$^{-/-}$ retinas that had been injected with LV-MYO7A(B) at P1 and dissected at P16. Cells were determined as corrected or not corrected by the apical localization of melanosomes, at a magnification that was too low to resolve the gold particles (hence there was no bias, based on labeling intensity). For quantification of the immunolabel, images of higher magnification were used, and all the gold particles in a complete section of each RPE cell were counted. The area of each cell's profile was determined using ImageJ software. For background labeling, the concentration of label in the outer nuclear layer was measured.

The concentration of opsin immunogold labeling in the connecting cilia of photoreceptor cells was determined by counting the gold particles along longitudinal profiles of connecting cilia and measuring the area of each profile. The labeling was quantified in four categories of photoreceptor cell: cells that were subjacent to corrected RPE cells in LV-MYO7A(B) treated retinas; cells that were distant from the injection site, where RPE melanosome distribution was not corrected in LV-MYO7A(B) treated retinas; those from MYO7A-null untreated retinas; and those from control (Myo7a$^{+/-}$) mice.

REFERENCES

1 Smith R J, Berlin C I, Hejtmancik J F, Keats B J, Kimberling W J, Lewis R A et al. Clinical diagnosis of the Usher syndromes. Usher Syndrome Consortium. Am J Med Genet 1994; 50: 32-38.
2 Keats B J, Corey D P. The usher syndromes. Am J Med Genet 1999; 89: 158-166.
3 Astuto L M, Weston M D, Carney C A, Hoover D M, Cremers C W, Wagenaar M et al. Genetic heterogeneity of Usher syndrome: analysis of 151 families with Usher type I. Am J Hum Genet 2000; 67: 1569-1574.
4 Bharadwaj A K, Kasztejna J P, Huq S, Berson E L, Dryja T P. Evaluation of the myosin VIIA gene and visual function in patients with Usher syndrome type I. Exp Eye Res 2000; 71: 173-181.
5 Ouyang X M, Yan D, Du L L, Hejtmancik J F, Jacobson S G, Nance W E et al. Characterization of Usher syndrome type I gene mutations in an Usher syndrome patient population. Hum Genet 2005; 116: 292-299.
6 Weil D, Blanchard S, Kaplan J, Guilford P, Gibson F, Walsh J et al. Defective myosin VIIA gene responsible for Usher syndrome type 1B. Nature 1995; 374: 60-61.
7 Hasson T, Heintzelman M B, Santos-Sacchi J, Corey D P, Mooseker M S. Expression in cochlea and retina of myosin VIIa, the gene product defective in Usher syndrome type 1B. Proc. Natl. Acad. Sci. USA 1995; 92: 9815-9819.
8 Wolfrum U, Liu X, Schmitt A, Udovichenko I P, Williams D S. Myosin VIIa as a common component of cilia and microvilli. Cell Motil Cytoskeleton 1998; 40: 261-271.
9 Gibbs D, Williams D S. Usher 1 protein complexes in the retina. Invest Opthalmol Vis Sci 2004; 45: e-letter (May 26).
10 El-Amraoui A, Schonn J S, Kussel-Andermann P, Blanchard S, Desnos C, Henry J P et al. MyRIP, a novel Rab effector, enables myosin VIIa recruitment to retinal melanosomes. EMBO Rep 2002; 3: 463-470.
11 Gibbs D, Azarian S M, Lillo C, Kitamoto J, Klomp A E, Steel K P et al. Role of myosin VIIa and Rab27a in the motility and localization of RPE melanosomes. J Cell Sci 2004; 117: 6473-6483.
12 Liu X, Vansant G, Udovichenko I P, Wolfrum U, Williams D S. Myosin VIIa, the product of the Usher 1B syndrome gene, is concentrated in the connecting cilia of photoreceptor cells. Cell Motil. Cytoskel. 1997; 37: 240-252.
13 Gibson F, Walsh J, Mburu P, Varela A, Brown K A, Antonio M et al. A type VII myosin encoded by mouse deafness gene shaker-1. Nature 1995; 374: 62-64.
14 Mburu P, Liu X Z, Walsh J, Saw D, Jamie M, Cope T V et al. Mutation analysis of the mouse myosin VIIA deafness gene. Genes Funct. 1997; 1: 191-203.
15 Hasson T, Walsh J, Cable J, Mooseker M S, Brown S D M, Steel K P. Effects of shaker-1 mutations on myosin-VIIa protein and mRNA expression. Cell Motility and the Cytoskeleton 1997; 37: 127-138.
16 Lillo C, Kitamoto J, Liu X, Quint E, Steel K P, Williams D S. Mouse models for Usher syndrome 1B. Adv Exp Med Biol 2003; 533: 143-150.
17 Liu X, Ondek B, Williams D S. Mutant myosin VIIa causes defective melanosome distribution in the RPE of shaker-1 mice. Nat. Genet. 1998; 19: 117-118.
18 Gibbs D, Kitamoto J, Williams D S. Abnormal phagocytosis by retinal pigmented epithelium that lacks myosin VIIa, the Usher syndrome 1B protein. Proc. Natl. Acad. Sci. USA 2003; 100: 6481-6486.
19 Futter C E, Ramalho J S, Jaissle G B, Seeliger M W, Seabra M C. The role of Rab27a in the regulation of melanosome distribution within retinal pigment epithelial cells. Mol Biol Cell 2004; 15: 2264-2275.
20 Young R W, Bok D. Participation of the retinal pigment epithelium in the rod outer segment renewal process. J. Cell Biol. 1969; 42: 392-403.
21 Bok D, Hall M O. The role of the pigment epithelium in the etiology of inherited retinal dystrophy in the rat. J Cell Biol 1971; 49: 664-682.
22 Schraermeyer U, Heimann K. Current understanding on the role of retinal pigment epithelium and its pigmentation. Pigment Cell Res 1999; 12: 219-236.
23 Liu X, Udovichenko I P, Brown S D M, Steel K P, Williams D S. Myosin VIIa participates in opsin transport through the photoreceptor cilium. J. Neurosci. 1999; 19: 6267-6274.
24 Acland G M, Aguirre G D, Ray J, Zhang Q, Aleman T S, Cideciyan A V et al. Gene therapy restores vision in a canine model of childhood blindness. Nat Genet 2001; 28: 92-95.
25 Narfstrom K, Katz M L, Bragadottir R, Seeliger M, Boulanger A, Redmond T M et al. Functional and structural recovery of the retina after gene therapy in the RPE65 null mutation dog. Invest Opthalmol Vis Sci 2003; 44: 1663-1672.
26 Dejneka N S, Surace E M, Aleman T S, Cideciyan A V, Lyubarsky A, Savchenko A et al. In utero gene therapy rescues vision in a murine model of congenital blindness. Mol Ther 2004; 9: 182-188.
27 Lai C M, Yu M J, Brankov M, Barnett N L, Zhou X, Redmond T M et al. Recombinant adeno-associated virus type 2-mediated gene delivery into the Rpe65−/− knockout mouse eye results in limited rescue. Genet Vaccines Ther 2004; 2: 3.
28 Pang J J, Chang B, Kumar A, Nusinowitz S, Noorwez S M, Li J et al. Gene Therapy Restores Vision-Dependent Behavior as Well as Retinal Structure and Function in a Mouse Model of RPE65 Leber Congenital Amaurosis. Mol Ther 2005.
29 Acland G M, Aguirre G D, Bennett J, Aleman T S, Cideciyan A V, Bennicelli J et al. Long-Term Restoration of Rod and Cone Vision by Single Dose rAAV-Mediated Gene Transfer to the Retina in a Canine Model of Childhood Blindness. Mol Ther 2005.

30. Vollrath D, Feng W, Duncan J L, Yasumura D, D'Cruz P M, Chappelow A et al. Correction of the retinal dystrophy phenotype of the RCS rat by viral gene transfer of Mertk. Proc Natl Acad Sci USA 2001; 98: 12584-12589.

31. Smith A J, Schlichtenbrede F C, Tschernutter M, Bainbridge J W, Thrasher A J, Ali R R. AAV-Mediated gene transfer slows photoreceptor loss in the RCS rat model of retinitis pigmentosa. Mol Ther 2003; 8: 188-195.

32. Tschernutter M, Schlichtenbrede F C, Howe S, Balaggan K S, Munro P M, Bainbridge J W et al. Long-term preservation of retinal function in the RCS rat model of retinitis pigmentosa following lentivirus-mediated gene therapy. Gene Ther 2005; 12: 694-701.

33. Kelley P M, Weston M D, Chen Z Y, Orten D J, Hasson T, Overbeck L D et al. The genomic structure of the gene defective in Usher syndrome type 1b (MYO7A). Genomics 1997; 40: 73-79.

34. Levy G, Levi-Acobas F, Blanchard S, Gerber S, Larget-Piet D, Chenal V et al. Myosin VIIA gene: heterogeneity of the mutations responsible for Usher syndrome type 1B. Hum Mol Genet 1997; 6: 111-116.

35. Verma I M, Weitzman M D. Gene therapy: twenty-first century medicine. Annu Rev Biochem 2005; 74: 711-738.

36. Dull T, Zufferey R, Kelly M, Mandel R J, Nguyen M, Trono D et al. A third-generation lentivirus vector with a conditional packaging system. J Virol 1998; 72: 8463-8471.

37. Pfeifer A, Brandon E P, Kootstra N, Gage F H, Verma I M. Delivery of the Cre recombinase by a self-deleting lentiviral vector: efficient gene targeting in vivo. Proc Natl Acad Sci USA 2001; 98: 11450-11455.

38. Aiken C. Pseudotyping human immunodeficiency virus type 1 (HIV-1) by the glycoprotein of vesicular stomatitis virus targets HIV-1 entry to an endocytic pathway and suppresses both the requirement for Nef and the sensitivity to cyclosporin A. J Virol 1997; 71: 5871-5877.

39. Burns J C, Friedmann T, Driever W, Burrascano M, Yee J K. Vesicular stomatitis virus G glycoprotein pseudotyped retroviral vectors: concentration to very high titer and efficient gene transfer into mammalian and nonmammalian cells. Proc Natl Acad Sci USA 1993; 90: 8033-8037.

40. Grieger J C, Samulski R J. Packaging capacity of adeno-associated virus serotypes: impact of larger genomes on infectivity and postentry steps. J Virol 2005; 79: 9933-9944.

41. el-Amraoui A, Sahly I, Picaud S, Sahel J, Abitbol M, Petit C. Human Usher 1B/mouse shaker-1: the retinal phenotype discrepancy explained by the presence/absence of myosin VIIA in the photoreceptor cells. Hum Mol Genet 1996; 5: 1171-1178.

42. Miyoshi H, Takahashi M, Gage F H, Verma I M. Stable and efficient gene transfer into the retina using an HIV-based lentiviral vector. Proc Natl Acad Sci USA 1997; 94: 10319-10323.

43. Takahashi M, Miyoshi H, Verma I M, Gage F H. Rescue from photoreceptor degeneration in the rd mouse by human immunodeficiency virus vector-mediated gene transfer. J Virol 1999; 73: 7812-7816.

44. Gruter O, Kostic C, Crippa S V, Perez M T, Zografos L, Schorderet D F et al. Lentiviral vector-mediated gene transfer in adult mouse photoreceptors is impaired by the presence of a physical barrier. Gene Ther 2005; 12: 942-947.

45. Bushman F D. Targeting survival: integration site selection by retroviruses and LTR-retrotransposons. Cell 2003; 115: 135-138.

46. Mitchell R S, Beitzel B F, Schroder A R, Shinn P, Chen H, Berry C C et al. Retroviral DNA integration: ASLV, HIV, and MLV show distinct target site preferences. PLoS Biol 2004; 2: E234.

47. Kuhn E J, Geyer P K. Genomic insulators: connecting properties to mechanism. Curr Opin Cell Biol 2003; 15: 259-265.

48. West A G, Fraser P. Remote control of gene transcription. Hum Mol Genet 2005; 14 (Suppl.): R101-111.

49. Yanez-Munoz R J, Balaggan K S, MacNeil A, Howe S J, Schmidt M, Smith A J et al. Effective gene therapy with nonintegrating lentiviral vectors. Nat Med 2006; 12: 348-353.

50. Weng J, Mata N L, Azarian S M, Tzekov R T, Birch D G, Travis G H. Insights into the function of Rim protein in photoreceptors and etiology of Stargardt's disease from the phenotype in abcr knockout mice. Cell 1999; 98: 13-23.

51. Johnson K R, Gagnon L H, Webb L S, Peters L L, Hawes N L, Chang B et al. Mouse models of USH1C and DFNB18: phenotypic and molecular analyses of two new spontaneous mutations of the Ush1c gene. Hum Mol Genet 2003; 12: 3075-3086.

52. Libby R T, Kitamoto J, Holme R H, Williams D S, Steel K P. Cdh23 mutations in the mouse are associated with retinal dysfunction but not retinal degeneration. Exp Eye Res 2003; 77: 731-739.

53. Ball S L, Bardenstein D, Alagramam K N. Assessment of retinal structure and function in Ames waltzer mice. Invest Opthalmol Vis Sci 2003; 44: 3986-3992.

54. Faktorovich E G, Steinberg R H, Yasumura D, Matthes M T, LaVail M M. Photoreceptor degeneration in inherited retinal dystrophy delayed by basic fibroblast growth factor. Nature 1990; 347: 83-86.

55. Zufferey R, Donello J E, Trono D, Hope T J. Woodchuck hepatitis virus posttranscriptional regulatory element enhances expression of transgenes delivered by retroviral vectors. J Virol 1999; 73: 2886-2892.

56. Orten D J, Weston M D, Kelley P M, Cremers C W, Wagenaar M, Jacobson S G et al. Analysis of DNA elements that modulate myosin VIIA expression in humans. Hum Mutat 1999; 14: 354.

57. Yang X-J. Preparation of Recombinant Retroviruses. In: Rakoczy E (ed). Vision Research Protocols. Human Press: Torowa, N.J., 2001, pp. 171-190.

58. Fields-Berry S C, Halliday A L, Cepko C L. A recombinant retrovirus encoding alkaline phosphatase confirms clonal boundary assignment in lineage analysis of murine retina. Proc Natl Acad Sci USA 1992; 89: 693-697.

59. Gibbs D, Williams DS. Isolation and culture of primary mouse retinal pigmented epithelial cells. Adv. Exp. Med. Biol. 2003; 533: 347-352.

A number of embodiments of the invention have been described. Nevertheless, it will be understood that various modifications may be made without departing from the spirit and scope of the invention. Accordingly, other embodiments are within the scope of the following claims.

What is claimed is:

1. A method for the treatment or amelioration of an Usher 1B syndrome ocular disease, comprising delivering subretinally to target cells by injection in at least one eye of a subject in need of said treatment, an expression vehicle comprising or consisting of a human immunodeficiency virus-1 (HIV-1) vector comprising:
   (i) a CMV-MYO7A promoter or an equivalent promoter active in a photoreceptor cell and/or a retinal pigment epithelium (RPE) cell in operable linkage with a polynucleotide sequence encoding a myosin VIIA (MYO7A) protein, and
   (ii) a chromosomal integration sequence, or a chromosomal integration sequence and a chromatin insulator, wherein the MYO7A protein is expressed in said target cells, thereby treating the Usher 1B syndrome ocular disease in said subject.

2. The method of claim 1 wherein the promoter comprises a VMD2 promoter.

3. The method of claim 1, wherein the subject is a human.

4. The method of claim 1, wherein the MYO7A protein is encoded by a human MYO7A gene.

5. The expression vehicle of claim 4, wherein the MYO7A protein is encoded by a human MYO7A gene comprising SEQ ID NO:1.

6. A method for treatment or amelioration of blindness due to Usher 1B syndrome in a subject, comprising:
   (a) providing an expression vehicle comprising or consisting of a human immunodeficiency virus-1 (HIV-1) vector comprising:
      (i) a CMV-MYO7A promoter active in a photoreceptor cell and/or a retinal pigment epithelium (RPE) cell in operable linkage with a polynucleotide sequence encoding a myosin VIIA (MYO7A) protein, and
      (ii) a chromosomal integration sequence, or a chromosomal integration sequence and a chromatin insulator, wherein the MYO7A protein is expressed in a photoreceptor cell or an RPE cell; and
   (b) delivering the expression vehicle to the photoreceptor cell or RPE cell in an amount sufficient to express the MYO7A protein in the photoreceptor cell or the RPE cell and thereby treat or ameliorate the Usher 1B syndrome blindness in said subject.

7. The method of claim 6, wherein the MYO7A protein is encoded by a human MYO7A gene.

8. The expression vehicle of claim 7, wherein the MYO7A protein is encoded by a human MYO7A gene comprising SEQ ID NO:1.

9. An expression vehicle comprising a human immunodeficiency virus (HIV) vector pseudotyped with the glycoprotein of vesicular stomatitis virus (VSV.G) and comprising a CMV-MYO7A promoter or an equivalent promoter active in a photoreceptor cell and/or a retinal pigment epithelium (RPE) cell in operable linkage with a polynucleotide sequence encoding a myosin VIIA (MYO7A) polypeptide.

10. The expression vehicle of claim 9, wherein the MYO7A protein is encoded by a human MYO7A gene.

11. The expression vehicle of claim 10, wherein the MYO7A protein is encoded by a human MYO7A gene comprising SEQ ID NO:1.

12. An ex vivo method for treatment or amelioration of blindness due to Usher 1B syndrome in a subject, comprising:
   (a) providing an expression vehicle comprising or consisting of a human immunodeficiency virus-1 (HIV-1) vector comprising:
      (i) a CMV-MYO7A promoter active in a photoreceptor cell and/or a retinal pigment epithelium (RPE) cell in operable linkage with a polynucleotide sequence encoding a myosin VIIA (MYO7A) protein, and
      (ii) a chromosomal integration sequence, or a chromosomal integration sequence and a chromatin insulator, wherein the MYO7A protein is expressed in a photoreceptor cell or an RPE cell;
   (b) providing the photoreceptor cell and/or the retinal pigment epithelium (RPE) cell;
   (c) delivering to the photoreceptor cell and/or the retinal pigment epithelium (RPE) cell the expression vehicle of step (a) in an amount sufficient to express the MYO7A protein in the photoreceptor cell or the RPE cell; and (d) delivering the photoreceptor cell and/or the retinal pigment epithelium (RPE) cell to an eye subretinally, thereby treating or ameliorating the Usher 1B syndrome in the subject.

13. An expression vehicle comprising an HIV vector pseudotyped with the glycoprotein of vesicular stomatitis virus (VSV.G) vector comprising a CMV-MYO7A active in a photoreceptor cell and/or a retinal pigment epithelium (RPE) cell in operable linkage with a polynucleotide sequence encoding a myosin VIIA (MYO7A) polypeptide.

14. The method of claim 13, wherein the MYO7A protein is encoded by a human MYO7A gene.

15. A method for the treatment or amelioration of an Usher 1B syndrome ocular disease, comprising delivering subretinally to target cells by injection in at least one eye of a subject in need of said treatment, an expression vehicle comprising or consisting of an HIV vector pseudotyped with the glycoprotein of vesicular stomatitis virus (VSV.G) vector comprising:
  (i) a CMV-MYO7A promoter active in a photoreceptor cell and/or a retinal pigment epithelium (RPE) cell in operable linkage with a polynucleotide sequence encoding a myosin VIIA (MYO7A) protein, and
  (ii) a chromosomal integration sequence, or a chromosomal integration sequence and a chromatin insulator,
  wherein the MYO7A protein is expressed in said target cells, thereby treating the Usher 1B syndrome ocular disease in said subject.

16. The method of claim 15, wherein the MYO7A protein is encoded by a human MYO7A gene.

17. A method for treatment or amelioration of blindness due to Usher 1B syndrome in a subject, comprising:
  (a) providing an expression vehicle comprising or consisting of an HIV vector pseudotyped with the glycoprotein of vesicular stomatitis virus (VSV.G) vector comprising:
    (i) a CMV-MYO7A promoter active in a photoreceptor cell and/or a retinal pigment epithelium (RPE) cell in operable linkage with a polynucleotide sequence encoding a myosin VIIA (MYO7A) protein, and
    (ii) a chromosomal integration sequence, or a chromosomal integration sequence and a chromatin insulator,
    wherein the MYO7A protein is expressed in a photoreceptor cell or an RPE cell; and
  (b) delivering the expression vehicle to the photoreceptor cell or RPE cell in an amount sufficient to express the MYO7A protein in the subretinally photoreceptor cell or the RPE cell and thereby treat or ameliorate the Usher 1B syndrome blindness in said subject.

18. The method of claim 17, wherein the MYO7A protein is encoded by a human MYO7A gene.

19. An ex vivo method for treatment or amelioration of blindness due to Usher 1B syndrome in a subject, comprising:
  (a) providing an expression vehicle comprising or consisting of an HIV vector pseudotyped with the glycoprotein of vesicular stomatitis virus (VSV.G) vector comprising:
    (i) a CMV-MYO7A promoter active in a photoreceptor cell and/or a retinal pigment epithelium (RPE) cell in operable linkage with a polynucleotide sequence encoding a myosin VIIA (MYO7A) protein, and
    (ii) a chromosomal integration sequence, or a chromosomal integration sequence and a chromatin insulator,
    wherein the MYO7A protein is expressed in a photoreceptor cell or an RPE cell;
  (b) providing the photoreceptor cell and/or the retinal pigment epithelium (RPE) cell;
  (c) delivering to the photoreceptor cell and/or the retinal pigment epithelium (RPE) cell the expression vehicle of step (a) in an amount sufficient to express the MYO7A protein in the photoreceptor cell or the RPE cell; and
  (d) delivering the photoreceptor cell and/or the retinal pigment epithelium (RPE) cell to an eye subretinally, thereby treating or ameliorating the Usher 1B syndrome in the subject.

20. The method of claim 19, wherein the MYO7A protein is encoded by a human MYO7A gene.

\* \* \* \* \*

SEQUENCE LISTING

<160> NUMBER OF SEQ ID NOS: 1

<210> SEQ ID NO 1
<211> LENGTH: 2175
<212> TYPE: PRT
<213> ORGANISM: Artificial Sequence
<220> FEATURE:
<223> OTHER INFORMATION: Synthetic construct

<400> SEQUENCE: 1

```
Met Val Ile Leu Gln Gln Gly Asp His Val Trp Met Asp Leu Arg Leu
  1               5                  10                  15

Gly Gln Glu Phe Asp Val Pro Ile Gly Ala Val Val Lys Leu Cys Asp
             20                  25                  30

Ser Gly Gln Val Gln Val Val Asp Asp Glu Asp Asn Glu His Trp Ile
         35                  40                  45

Ser Pro Gln Asn Ala Thr His Ile Lys Pro Met His Pro Thr Ser Val
     50                  55                  60

His Gly Val Glu Asp Met Ile Arg Leu Gly Asp Leu Asn Glu Ala Gly
 65                  70                  75                  80

Ile Leu Arg Asn Leu Leu Ile Arg Tyr Arg Asp His Leu Ile Tyr Thr
                 85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350
```

-continued

```
Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
    450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
        515                 520                 525

Asn Ser Gln His Lys Leu Asn Ala Asn Tyr Ile Pro Pro Lys Asn Asn
    530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
    610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg Arg Ala Gly Tyr
            660                 665                 670

Pro Ile Arg Tyr Ser Phe Val Glu Phe Val Glu Arg Tyr Arg Val Leu
        675                 680                 685

Leu Pro Gly Val Lys Pro Ala Tyr Lys Gln Gly Asp Leu Arg Gly Thr
    690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                725                 730                 735

Glu Val Glu Arg Asp Lys Ala Ile Thr Asp Arg Val Ile Leu Leu Gln
            740                 745                 750

Lys Val Ile Arg Gly Phe Lys Asp Arg Ser Asn Phe Leu Lys Leu Lys
        755                 760                 765
```

-continued

```
Asn Ala Ala Thr Leu Ile Gln Arg His Trp Arg Gly His Asn Cys Arg
            770                 775                 780

Lys Asn Tyr Gly Leu Met Arg Leu Gly Phe Leu Arg Leu Gln Ala Leu
785                 790                 795                 800

His Arg Ser Arg Lys Leu His Gln Gln Tyr Arg Leu Ala Arg Gln Arg
                805                 810                 815

Ile Ile Gln Phe Gln Ala Arg Cys Arg Ala Tyr Leu Val Arg Lys Ala
            820                 825                 830

Phe Arg His Arg Leu Trp Ala Val Leu Thr Val Gln Ala Tyr Ala Arg
            835                 840                 845

Gly Met Ile Ala Arg Arg Leu His Gln Arg Leu Arg Ala Glu Tyr Leu
    850                 855                 860

Trp Arg Leu Glu Ala Glu Lys Met Arg Leu Ala Glu Glu Glu Lys Leu
865                 870                 875                 880

Arg Lys Glu Met Ser Ala Lys Lys Ala Lys Glu Glu Ala Glu Arg Lys
                885                 890                 895

His Gln Glu Arg Leu Ala Gln Leu Ala Arg Glu Asp Ala Glu Arg Glu
            900                 905                 910

Leu Lys Glu Lys Glu Ala Ala Arg Arg Lys Lys Glu Leu Leu Glu Gln
            915                 920                 925

Met Glu Arg Ala Arg His Glu Pro Val Asn His Ser Asp Met Val Asp
    930                 935                 940

Lys Met Phe Gly Phe Leu Gly Thr Ser Gly Gly Leu Pro Gly Gln Glu
945                 950                 955                 960

Gly Gln Ala Pro Ser Gly Phe Glu Asp Leu Glu Arg Gly Arg Arg Glu
                965                 970                 975

Met Val Glu Glu Asp Leu Asp Ala Ala Leu Pro Leu Pro Asp Glu Asp
            980                 985                 990

Glu Glu Asp Leu Ser Glu Tyr Lys Phe Ala Lys Phe Ala Ala Thr Tyr
            995                 1000                1005

Phe Gln Gly Thr Thr Thr His Ser Tyr Thr Arg Arg Pro Leu Lys Gln
        1010                1015                1020

Pro Leu Leu Tyr His Asp Asp Glu Gly Asp Gln Leu Ala Ala Leu Ala
1025                1030                1035                1040

Val Trp Ile Thr Ile Leu Arg Phe Met Gly Asp Leu Pro Glu Pro Lys
                1045                1050                1055

Tyr His Thr Ala Met Ser Asp Gly Ser Glu Lys Ile Pro Val Met Thr
            1060                1065                1070

Lys Ile Tyr Glu Thr Leu Gly Lys Lys Thr Tyr Lys Arg Glu Leu Gln
        1075                1080                1085

Ala Leu Gln Gly Glu Gly Glu Ala Gln Leu Pro Glu Gly Gln Lys Lys
            1090                1095                1100

Ser Ser Val Arg His Lys Leu Val His Leu Thr Leu Lys Lys Lys Ser
1105                1110                1115                1120

Lys Leu Thr Glu Glu Val Thr Lys Arg Leu His Asp Gly Glu Ser Thr
                1125                1130                1135

Val Gln Gly Asn Ser Met Leu Glu Asp Arg Pro Thr Ser Asn Leu Glu
            1140                1145                1150

Lys Leu His Phe Ile Ile Gly Asn Gly Ile Leu Arg Pro Ala Leu Arg
        1155                1160                1165

Asp Glu Ile Tyr Cys Gln Ile Ser Lys Gln Leu Thr His Asn Pro Ser
    1170                1175                1180

Lys Ser Ser Tyr Ala Arg Gly Trp Ile Leu Val Ser Leu Cys Val Gly
```

-continued

```
              1185                1190                1195                1200

Cys Phe Ala Pro Ser Glu Lys Phe Val Lys Tyr Leu Arg Asn Phe Ile
                1205                1210                1215

His Gly Gly Pro Pro Gly Tyr Ala Pro Tyr Cys Glu Glu Arg Leu Arg
                1220                1225            1230

Arg Thr Phe Val Asn Gly Thr Arg Thr Gln Pro Pro Ser Trp Leu Glu
            1235                1240                1245

Leu Gln Ala Thr Lys Ser Lys Lys Pro Ile Met Leu Pro Val Thr Phe
        1250                1255                1260

Met Asp Gly Thr Thr Lys Thr Leu Leu Thr Asp Ser Ala Thr Thr Ala
1265                1270                1275                1280

Lys Glu Leu Cys Asn Ala Leu Ala Asp Lys Ile Ser Leu Lys Asp Arg
                1285                1290                1295

Phe Gly Phe Ser Leu Tyr Ile Ala Leu Phe Asp Lys Val Ser Ser Leu
                1300                1305                1310

Gly Ser Gly Ser Asp His Val Met Asp Ala Ile Ser Gln Cys Glu Gln
                1315                1320                1325

Tyr Ala Lys Glu Gln Gly Ala Gln Glu Arg Asn Ala Pro Trp Arg Leu
            1330                1335                1340

Phe Phe Arg Lys Glu Val Phe Thr Pro Trp His Ser Pro Ser Glu Asp
1345                1350                1355                1360

Asn Val Ala Thr Asn Leu Ile Tyr Gln Gln Val Val Arg Gly Val Lys
                1365                1370                1375

Phe Gly Glu Tyr Arg Cys Glu Lys Glu Asp Leu Ala Glu Leu Ala
                1380                1385                1390

Ser Gln Gln Tyr Phe Val Asp Tyr Gly Ser Glu Met Ile Leu Glu Arg
            1395                1400                1405

Leu Leu Asn Leu Val Pro Thr Tyr Ile Pro Arg Glu Ile Thr Pro
        1410                1415                1420

Leu Lys Thr Leu Glu Lys Trp Ala Gln Leu Ala Ile Ala Ala His Lys
1425                1430                1435                1440

Lys Gly Ile Tyr Ala Gln Arg Arg Thr Asp Ala Gln Lys Val Lys Glu
                1445                1450                1455

Asp Val Val Ser Tyr Ala Arg Phe Lys Trp Pro Leu Leu Phe Ser Arg
                1460                1465                1470

Phe Tyr Glu Ala Tyr Lys Phe Ser Gly Pro Ser Leu Pro Lys Asn Asp
            1475                1480                1485

Val Ile Val Ala Val Asn Trp Thr Gly Val Tyr Phe Val Asp Glu Gln
                1490                1495                1500

Glu Gln Val Leu Leu Glu Leu Ser Phe Pro Glu Ile Met Ala Val Ser
1505                1510                1515                1520

Ser Ser Arg Gly Ala Lys Thr Thr Ala Pro Ser Phe Thr Leu Ala Thr
                1525                1530                1535

Ile Lys Gly Asp Glu Tyr Thr Phe Thr Ser Ser Asn Ala Glu Asp Ile
                1540                1545                1550

Arg Asp Leu Val Val Thr Phe Leu Glu Gly Leu Arg Lys Arg Ser Lys
            1555                1560                1565

Tyr Val Val Ala Leu Gln Asp Asn Pro Asn Pro Ala Gly Glu Glu Ser
        1570                1575                1580

Gly Phe Leu Ser Phe Ala Lys Gly Asp Leu Ile Ile Leu Asp His Asp
1585                1590                1595                1600

Thr Gly Glu Gln Val Met Asn Ser Gly Trp Ala Asn Gly Ile Asn Glu
                1605                1610                1615
```

-continued

```
Arg Thr Lys Gln Arg Gly Asp Phe Pro Thr Asp Ser Val Tyr Val Met
                1620                1625                1630

Pro Thr Val Thr Met Pro Pro Arg Glu Ile Val Ala Leu Val Thr Met
                1635                1640                1645

Thr Pro Asp Gln Arg Gln Asp Val Val Arg Leu Leu Gln Leu Arg Thr
                1650                1655                1660

Ala Glu Pro Glu Val Arg Ala Lys Pro Tyr Thr Leu Glu Glu Phe Ser
1665                1670                1675                1680

Tyr Asp Tyr Phe Arg Pro Pro Lys His Thr Leu Ser Arg Val Met
                1685                1690                1695

Val Ser Lys Ala Arg Gly Lys Asp Arg Leu Trp Ser His Thr Arg Glu
                1700                1705                1710

Pro Leu Lys Gln Ala Leu Leu Lys Lys Leu Leu Gly Ser Glu Glu Leu
                1715                1720                1725

Ser Gln Glu Ala Cys Leu Ala Phe Ile Ala Val Leu Lys Tyr Met Gly
                1730                1735                1740

Asp Tyr Pro Ser Lys Arg Thr Arg Ser Val Asn Glu Leu Thr Asp Gln
1745                1750                1755                1760

Ile Phe Glu Gly Pro Leu Lys Ala Glu Pro Leu Lys Asp Glu Ala Tyr
                1765                1770                1775

Val Gln Ile Leu Lys Gln Leu Thr Asp Asn His Ile Arg Tyr Ser Glu
                1780                1785                1790

Glu Arg Gly Trp Glu Leu Leu Trp Leu Cys Thr Gly Leu Phe Pro Pro
                1795                1800                1805

Ser Asn Ile Leu Leu Pro His Val Gln Arg Phe Leu Gln Ser Arg Lys
                1810                1815                1820

His Cys Pro Leu Ala Ile Asp Cys Leu Gln Arg Leu Gln Lys Ala Leu
1825                1830                1835                1840

Arg Asn Gly Ser Arg Lys Tyr Pro Pro His Leu Val Glu Val Glu Ala
                1845                1850                1855

Ile Gln His Lys Thr Thr Gln Ile Phe His Lys Val Tyr Phe Pro Asp
                1860                1865                1870

Asp Thr Asp Glu Ala Phe Glu Val Glu Ser Ser Thr Lys Ala Lys Asp
                1875                1880                1885

Phe Cys Gln Asn Ile Ala Thr Arg Leu Leu Leu Lys Ser Ser Glu Gly
                1890                1895                1900

Phe Ser Leu Phe Val Lys Ile Ala Asp Lys Val Leu Ser Val Pro Glu
1905                1910                1915                1920

Asn Asp Phe Phe Phe Asp Phe Val Arg His Leu Thr Asp Trp Ile Lys
                1925                1930                1935

Lys Ala Arg Pro Ile Lys Asp Gly Ile Val Pro Ser Leu Thr Tyr Gln
                1940                1945                1950

Val Phe Phe Met Lys Lys Leu Trp Thr Thr Thr Val Pro Gly Lys Asp
                1955                1960                1965

Pro Met Ala Asp Ser Ile Phe His Tyr Tyr Gln Glu Leu Pro Lys Tyr
                1970                1975                1980

Leu Arg Gly Tyr His Lys Cys Thr Arg Glu Glu Val Leu Gln Leu Gly
1985                1990                1995                2000

Ala Leu Ile Tyr Arg Val Lys Phe Glu Glu Asp Lys Ser Tyr Phe Pro
                2005                2010                2015

Ser Ile Pro Lys Leu Leu Arg Glu Leu Val Pro Gln Asp Leu Ile Arg
                2020                2025                2030
```

```
                                                      -continued

Gln Val Ser Pro Asp Asp Trp Lys Arg Ser Ile Val Ala Tyr Phe Asn
        2035                2040                2045

Lys His Ala Gly Lys Ser Lys Glu Glu Ala Lys Leu Ala Phe Leu Lys
    2050                2055                2060

Leu Ile Phe Lys Trp Pro Thr Phe Gly Ser Ala Phe Phe Glu Gln Thr
2065                2070                2075                2080

Thr Glu Pro Asn Phe Pro Glu Ile Leu Leu Ile Ala Ile Asn Lys Tyr
                2085                2090                2095

Gly Val Ser Leu Ile Asp Pro Lys Thr Lys Asp Ile Leu Thr Thr His
            2100                2105                2110

Pro Phe Thr Lys Ile Ser Asn Trp Ser Ser Gly Asn Thr Tyr Phe His
        2115                2120                2125

Ile Thr Ile Gly Asn Leu Val Arg Gly Ser Lys Leu Leu Cys Glu Thr
    2130                2135                2140

Ser Leu Gly Tyr Lys Met Asp Asp Leu Leu Thr Ser Tyr Ile Ser Gln
2145                2150                2155                2160

Met Leu Thr Ala Met Ser Lys Gln Arg Gly Ser Arg Ser Gly Lys
                2165                2170                2175
```